US012687495B2

(12) United States Patent
Chien

(10) Patent No.: US 12,687,495 B2
(45) Date of Patent: Jul. 21, 2026

(54) SINGLE CELL SELECTION AND ISOLATION

(71) Applicant: ERASMUS UNIVERSITY MEDICAL CENTER ROTTERDAM, Rotterdam (NL)

(72) Inventor: Miao-Ping Chien, Rotterdam (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 959 days.

(21) Appl. No.: 17/424,304

(22) PCT Filed: Jan. 21, 2020

(86) PCT No.: PCT/NL2020/050028

§ 371 (c)(1),
(2) Date: Jul. 20, 2021

(87) PCT Pub. No.: WO2020/153837

PCT Pub. Date: Jul. 30, 2020

(65) Prior Publication Data

US 2022/0090007 A1 Mar. 24, 2022

(30) Foreign Application Priority Data

Jan. 22, 2019 (EP) .................................... 19153098

(51) Int. Cl.
*G01N 21/64* (2006.01)
*C09B 11/24* (2006.01)
(Continued)

(52) U.S. Cl.
CPC ........ *G01N 21/6458* (2013.01); *C09B 11/245* (2013.01); *C12M 47/04* (2013.01);
(Continued)

(58) Field of Classification Search
CPC ..... C12N 5/0081; C09B 11/245; C09B 11/08; C09B 11/24; C09B 57/02; C12M 47/04;
(Continued)

(56) References Cited

U.S. PATENT DOCUMENTS

2005/0042662 A1 2/2005 Li et al.
2016/0208308 A1 7/2016 Cohen et al.

OTHER PUBLICATIONS

Zhang et al, "Live-Cell Imaging at the Nanoscale with Bioconjugatable and Photoactivatable Fluorophores", Bioconjugate Chemistry, 2020, 31, 1052-1062. (Year: 2020).*

(Continued)

*Primary Examiner* — Christopher L Chin
(74) *Attorney, Agent, or Firm* — Hoffmann and Baron, LLP

(57) ABSTRACT

According to one method, a sample with cells contains a phototagging agent. The sample is imaged to identify at least one target cell to be isolated. The identified target cell in the sample is selectively irradiated with photo-activating light for selectively activating the phototagging agent in the target cell to change its fluorescence response. The irradiated target cell is isolated from other cells in the sample based on a difference in its fluorescence response compared to non-activated phototagging agent in the other cells. Further aspects are directed to a corresponding microscope system and chemical compound for use as the phototagging agent.

20 Claims, 12 Drawing Sheets

(51) Int. Cl.
*C12M 1/00* (2006.01)
*C12N 5/00* (2006.01)
*G01N 15/14* (2006.01)
*G01N 15/1434* (2024.01)
*G01N 33/50* (2006.01)
*G02B 21/00* (2006.01)

(52) U.S. Cl.
CPC ....... *C12N 5/0081* (2013.01); *G01N 15/1425* (2013.01); *G01N 15/1434* (2013.01); *G01N 33/5005* (2013.01); *G02B 21/0048* (2013.01); *G02B 21/0076* (2013.01)

(58) Field of Classification Search
CPC ........... G01N 15/1425; G01N 15/1434; G01N 21/6458; G01N 33/5005; G01N 2015/1006; G01N 33/582; G02B 21/0048; G02B 21/0076; G02B 21/0032; G02B 21/361; G02B 21/004
USPC ........ 356/317, 318, 402; 359/368, 385, 389; 422/82.08; 435/288.7; 436/63, 172, 537, 436/800, 805
See application file for complete search history.

(56) References Cited

OTHER PUBLICATIONS

Gould et al, "Imaging biological structures with fluorescence photoactivation localization microscopy", Nature Protocols, vol. 4, No. 3, 2009, 291-308. (Year: 2009).*
Patterson et al, "Developing Photoactivated Localization Microscopy (PALM)", IEEE, 2007, 940-943. (Year: 2007).*
Hauke, S. et al., "Specific protein labeling with caged fluorophores for dual-color imaging and super-resolution microscopy in living cells." Chemical Science, 2017, pp. 559-566, vol. 8.
Hu, P. et al., "Single Cell Isolation and Analysis.", Frontiers in Cell and Developmental Biology, 2016, article 116, vol. 4.
Valihrach, L. et al., "Platforms for Single-Cell Collection and Analysis", International Journal of Molecular Sciences, 2018, article 807, vol. 19.
Wysocki, L.M. et al., "Facile and General Synthesis of Photoactivatable Xanthene Dyes." Angewandte Chemie (International ed. in English), 2011, pp. 11206-11209, vol. 50.
Zhao Y. et al., "New Caged Coumarin Fluorophores with Extraordinary Uncaging Cross Sections Suitable for Biological Imaging Applications." Journal of the American Chemical Society, 2004, pgs. 4653-4663, vol. 126.
Raymo, Françisco M. "Photoactivatable fluorophores." International Scholarly Research Notices 2012 (2012).
Fouassier, Jean-Pierre, et al. "Dyes as photoinitiators or photosensitizers of polymerization reactions." Materials 3.12 (2010): 5130-5142.
Banala, Sambashiva, et al. "A caged, localizable rhodamine derivative for superresolution microscopy." ACS chemical biology 7.2 (2012): 289-293.
Gross, Andre, et al. "Technologies for single-cell isolation." International journal of molecular sciences 16.8 (2015): 16897-16919.
Klán, Petr, et al. "Photoremovable protecting groups in chemistry and biology: reaction mechanisms and efficacy." Chemical reviews 113.1 (2013): 119-191. (Parts 1-3).
Ottl, Johannes, Daniela Gabriel, and Gerard Marriott. "Preparation and photoactivation of caged fluorophores and caged proteins using a new class of heterobifunctional, photocleavable cross-linking reagents." Bioconjugate chemistry 9.2 (1998): 143-151.

* cited by examiner

Caged rhodamine

Thioxanthone

Caged rhodamine with thioxanthone

Uncaged rhodamine with thioxanthone

Cells incubated with 15 μM phototagging agent
(caged rhodamine with thioxanthone)

Cells incubated with 15 μM phototagging agent
(caged rhodamine without thioxanthone)

SINGLE CELL SELECTION AND ISOLATION

CROSS-REFERENCE TO RELATED APPLICATIONS

This application is a National Phase application of International Application No. PCT/NL2020/050028 filed Jan. 21, 2020 which claims priority to European Patent Application No. EP 19153098.9 filed Jan. 22, 2019, the disclosures of which are incorporated herein by reference.

TECHNICAL FIELD AND BACKGROUND

The present disclosure relates to a method for isolating cells in a sample, a microscope system for performing such method, and a chemical compound for use in such method and/or system.

As background, U.S. Pat. No. 10,077,463 B2 provides photochemical crosslinkers and photocleavable crosslinkers and their uses in methods for cell selection from cell cultures. The photochemical crosslinkers comprise a fluorescent dye and a radical generator. The photocleavable crosslinkers comprise a photocleavable linker linking two organic groups to each other. Also provided are systems for imaging cells comprising a plurality of cells crosslinked to extracellular matrix proteins using a crosslinker as described, an imaging apparatus, an illuminating apparatus, and software for image processing.

There is yet a need for methods, systems, and compounds providing synergetic improvements in versatility and efficiency for selecting and isolating cells in different types of samples (e.g., two-dimensional cell cultures and three-dimensional tissues, biopsies, or spheroid cultures) while avoiding cell damage.

SUMMARY

Some aspects relate to a method for isolating cells. A sample with cells containing a phototagging agent is provided. The sample is imaged to identify at least one target cell to be isolated. The identified target cell in the sample is selectively irradiated with photo-activating light for selectively activating the phototagging agent in the target cell to change its fluorescence response (e.g. from a non-fluorescent to fluorescent state). The irradiated target cell is isolated from other cells in the sample based on a difference in its fluorescence response compared to non-activated phototagging agent in the other cells.

Other or further aspects relate to a microscope system. A sample holder is configured to hold a sample with cells containing a phototagging agent. One or more excitation light sources are configured to illuminate the sample with light. A photon or light detector is configured to detect emitted photons of the illuminated sample and to form an image for spatially resolving the cells. A controller or program is implemented to determine the target cell from the recorded images after analysis and to determine the coordinates of the corresponding target cell in the sample based on the target selection. Beam patterning and/or steering optics are configured to receive the target coordinates of the target cell, and selectively direct the photo-activating light to irradiate a target location of the target cell in the sample based on the target coordinates. One or more photo-activation light sources are configured to generate photo-activating light for activating the phototagging agent inside of the target cell to change its fluorescence response.

Other or further aspects relate to a chemical compound comprising a caged fluorophore moiety conjugated to a photosensitizer moiety. This can be used, e.g., as a phototagging agent in the methods or systems described herein. Caged fluorophores or other photoactivatable fluorophores or proteins can be also used in the methods described herein to isolate target cells.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
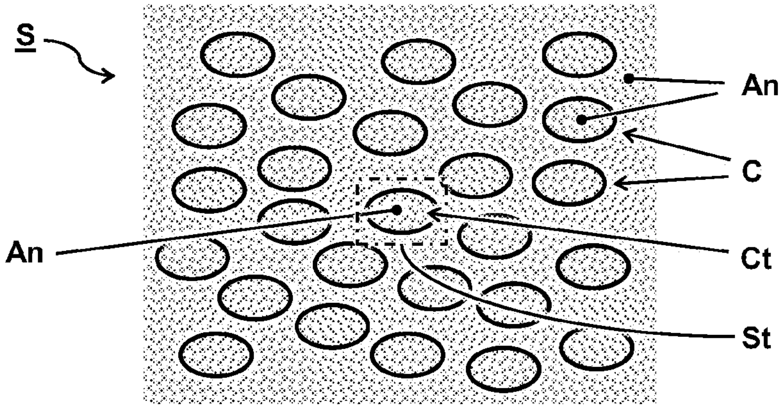
FIGS. 1A-1C illustrate a method for isolating cells.

Terminology used for describing particular embodiments is not intended to be limiting of the invention. As used herein, the singular forms “a”, “an” and “the” are intended to include the plural forms as well, unless the context clearly indicates otherwise. The term “and/or” includes any and all combinations of one or more of the associated listed items. It will be understood that the terms “comprises” and/or “comprising” specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise, it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1B:
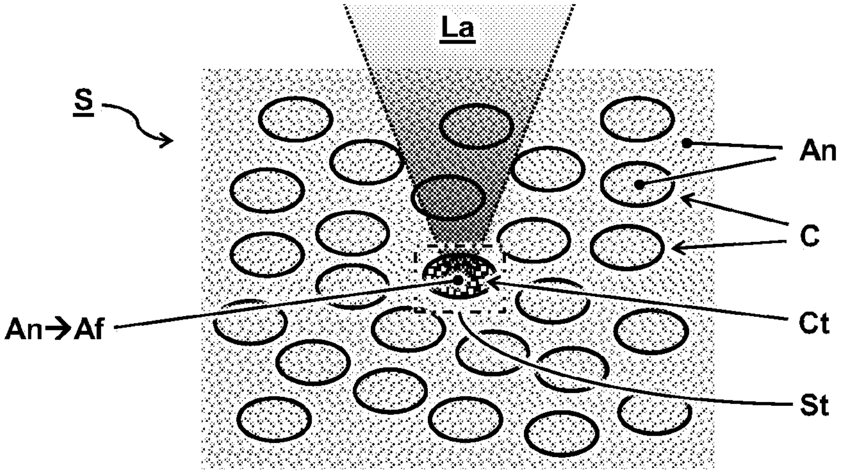
Figure 1C:
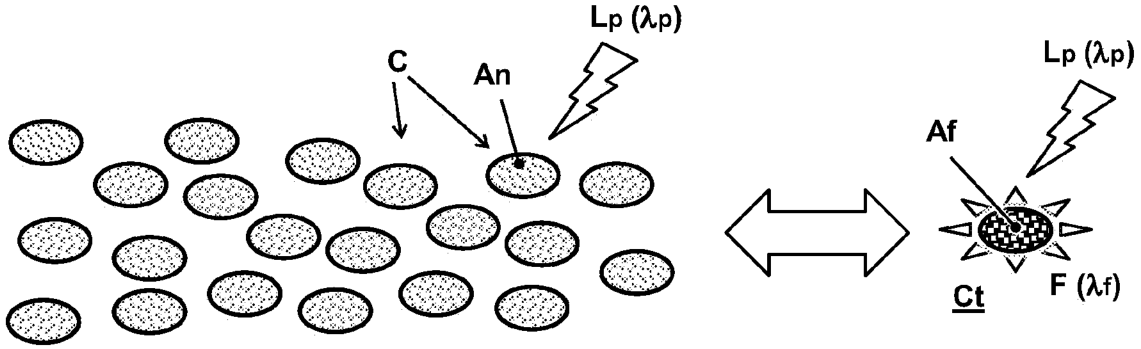

FIGS. 1A-1C illustrate a method for isolating cells. In some embodiments, a sample S with cells C contains a phototagging agent An. In other or further embodiments, the sample S is imaged to identify at least one target cell Ct to be isolated. In other or further embodiments, irradiating the identified target cell Ct in the sample S is irradiated with photo-activating light La. This can be used for selectively activating the phototagging agent in the target cell Ct. Accordingly, the phototagging agent may change its fluorescence response F. In some embodiments, the irradiated target cell Ct is isolated from other cells in the sample based on a difference in its fluorescence response F, e.g. compared to non-activated phototagging agent An in the other cells C.

In a preferred embodiment, the activation causes a structural change An→Af of the phototagging agent An contained in the target cell Ct. In some embodiments, as described herein, the activating of the phototagging agent An causes an increase in its fluorescence response F. For example, the activation converts the phototagging agent from an initially non-fluorescent molecule An to a fluorescent molecule Af, or from a relatively low-fluorescent to a relatively high-fluorescent molecule. Accordingly, the target cell Ct may be isolated based on its relatively high fluorescence response F compared to the other cells. It can also be envisaged that the activation causes a decrease in the fluorescence response F of the phototagging agent An. In this case, the target cell Ct may be isolated based on its relatively low fluorescence response F compared to the other cells. It can also be envisaged that the activation causes higher or lower fluorescence response in photoactivated or photoconverted fluorescent proteins acting as the phototagging agent.

In a preferred embodiment, the change in the fluorescence response F caused by the activation or conversion is substantially permanent, or at least sufficiently long lasting to allow the subsequent isolating of the target cell Ct based on the difference in the fluorescence response F. For example, the phototagging agent An comprises a caged fluorophore, wherein the photo-activating light La causes an uncaging of the fluorophore, as described herein. The uncaging may permanently increase the subsequent fluorescence response F of the agent. Also other ways may be envisaged to activate a phototagging agent An to cause permanent or long lasting change of its fluorescence response F. Preferably, the change in response lasts more than one second, more than five seconds, more than ten seconds, more than one minute, more than five minutes, or longer, e.g. indefinitely. The longer the change in fluorescence response can last, the more time this gives between the activation/selection and subsequent isolation based on the changed response. While the preferred use of a caged fluorophore (most preferably a photosensitized variant) can have particular advantages, it will be appreciated that the single cell selection pipeline as described herein can also work (with at least some of the same or similar advantages) for any other or further kind of photoactivatable agent or protein, photo-converted protein, et cetera.

In one embodiment, the photo-activating light La predominantly or exclusively activates the phototagging agent in the one or more identified target cells Ct with minimal or no activation of the phototagging agent in other (surrounding) cells. For example, more than fifty percent of the phototagging agent in the sample S being activated by the photo-activating light La is contained within the identified one or more target cells Ct, preferably at least eighty or ninety percent, or even up to a hundred percent. The more the activation is limited to the phototagging agent contained in the target cell, the easier may be its subsequent isolation based on the distinct fluorescence response F. Of course, even with less than perfect activation, it may still be possible to isolate the target cell Ct based on its relative fluorescence response (e.g. higher intensity) compared to other, lesser activated, cells.

In a preferred embodiment, the phototagging agent An is cell-permeable, at least before it is activated. This allows the phototagging agent An to be easily added to any sample with cells, e.g. without damaging the cells. In another or further embodiment, a cell-permeable or impermeable phototagging agent An is produced in the cells C. For example, the phototagging agent An may be an already occurring substance in the cells, or the cells may be modified to produce the phototagging agent An and/or this may be a photoactivated or photoconverted fluorescent protein. It can also be envisaged that a permeable or impermeable phototagging agent An is forced, e.g. injected, into the cells. In some embodiments, the phototagging agent loses some or all of its cell-permeability after it is activated. While not necessary, this may help to retain the activated agent in the cell during isolation.

Figure 2A:
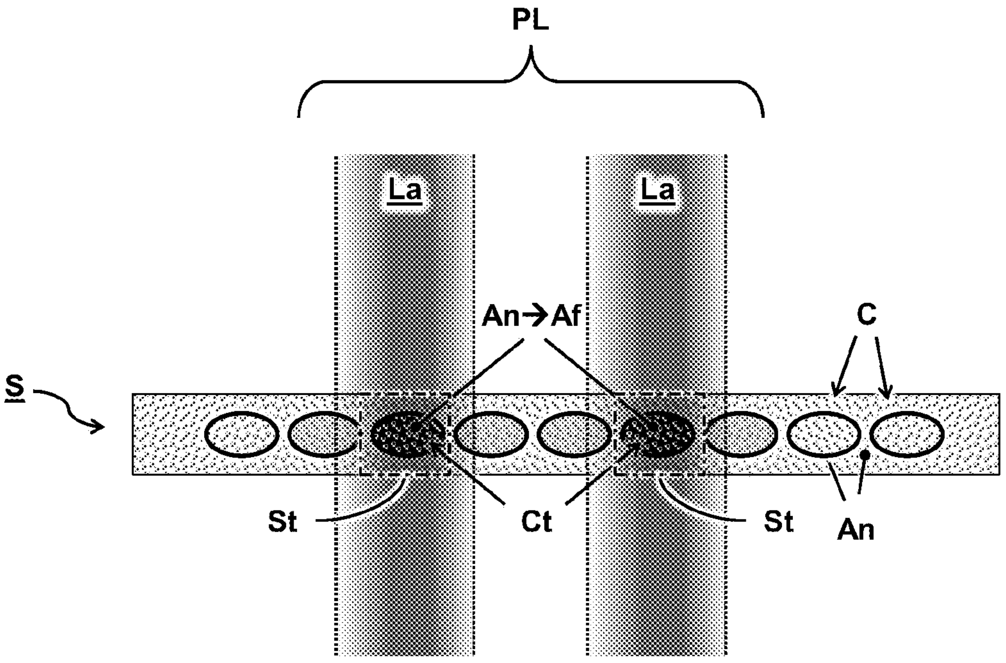
FIG. 2A illustrates irradiating a target cell in an essentially two-dimensional sample.

FIG. 2A illustrates irradiating a target cell Ct in an essentially two-dimensional sample S. In some embodiments, the sample S essentially consists of only a single layer of cells. This makes it relatively easy to exclusively irradiate one or more target cells Ct in the single layer, e.g. because the beam of photo-activating light La does not need to traverse other (non-targeted) cells. For example, the beam of light may be substantially directed normal to the layer of cells, as shown, or at some angle. In some embodiments, the photo-activating light La is delivered by a collimated beam. For example, a width of the beam may be relatively small or on the order of the target cell size.

In some embodiments (not shown), a light pattern is projected onto multiple target cells. For example, the light pattern comprises multiple (disjointed) light spots at different positions of the sample. In this way multiple target cells may be simultaneously activated for subsequent isolation. In some embodiments, the light pattern is projected by multiple light beams, e.g. using beam splitters. In another or further embodiment, the light pattern may be projected by masking one or more light beams. In a preferred embodiment, as described in further detail below, the light pattern is produced by a digital mirror device (DMD) or other opto-electromechnical devices. Also other devices, such as galvanometer mirrors or Galvo mirrors, can be used to direct the light to one or more spots. In some embodiments, the sample is an essentially two dimensional sample with a single layer of cells and the phototagging agent is activated by applying a pattern of the photo-activating light onto the sample.

Figure 2B:
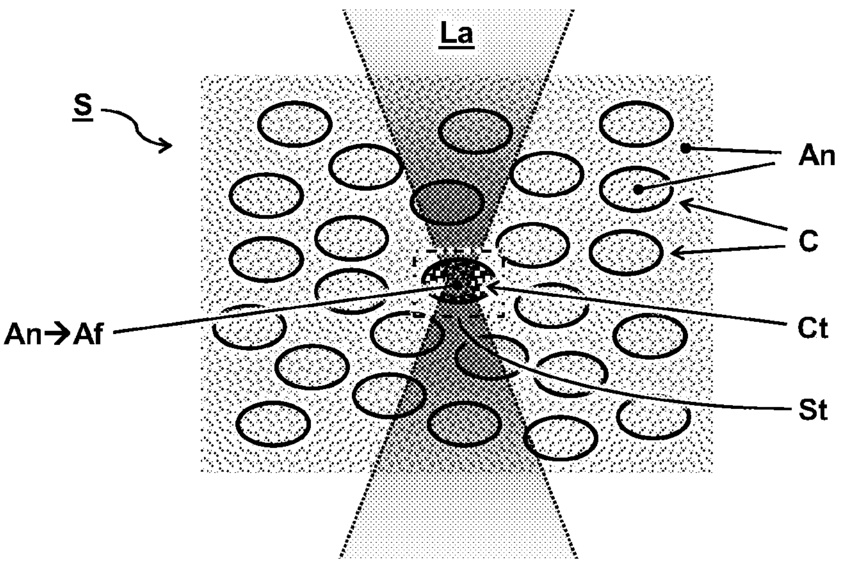
FIG. 2B illustrates irradiating a target cell in an essentially three-dimensional sample.

FIG. 2B illustrates irradiating a target cell Ct in an essentially three-dimensional sample S. In some embodiments, a beam of the photo-activating light La is focused onto one or more target cell Ct in a two or three dimensional sample S. The light beam may be relatively small at the focal spot so the photo-activating light La can be better targeted onto the target cell Ct without irradiating surrounding cells. Also, a light intensity of the photo-activating light La at a focal point of the beam may be relatively high. So the photo-activation may be more prominent at the focal point. To further increase intensity and/or to obtain selective optical sectioning (activate specific cells in three-dimensional samples), the photo-activating light La may be generated by a pulsed light source, such as a pulsed or femtosecond laser. For example, the momentary light intensity during a laser pulse can be much higher than in a continuous wave laser.

In some embodiments, an increased light intensity produced by a focal spot, laser pulse, or combination thereof, may enable unique processes to occur which do not take place at lower intensities. For example, the relatively high intensity may enable multi-photon absorption. It will be appreciated that this can be used to select the target location St of one or more cell in three dimensions. For example, two coordinates may be determined by adjusting a position or direction of the beam, and one coordinate may be determined by adjusting the beam focal position (along the beam direction). Instead of a focused light spot a locally increased intensity may also be achieved, e.g. crossing two or more beams at a target position in the sample S. In some embodiments, the sample is an essentially three dimensional sample with multiple layers of cells along a beam direction. In other or further embodiments, the phototagging agent An is activated by two-photon or multi-photon absorption exclusively at a focal spot of the photo-activating light La, e.g. in a subset of one or more (not all) of the layers.

In one embodiment, the photo-activating light La may comprise a source wavelength λs (e.g. output from a light source) that is above a (maximum) activation wavelength λa at which the phototagging agent An can be activated. In a further embodiment, the source wavelength λs is below an integer multiple, e.g. double, the (maximum) activation wavelength, i.e. $\lambda s \leq 2 \cdot \lambda a$, so the phototagging agent An can still be activated, e.g. by two photon absorption. For example, photo-activating light La is produced by a focal spot of an eight hundred nanometer pulsed laser, where the phototagging agent An is activated by four hundred nanometer continuous wave (CW) light (half the wavelength, double the energy). In a preferred embodiment, the phototagging agent An comprises a photosensitizer. Accordingly this may allow the use of photo-activating light La in a (visible) wavelength range, e.g. above 400 nm. Other photoactivated fluorophores or proteins are also possible.

Figure 3A:
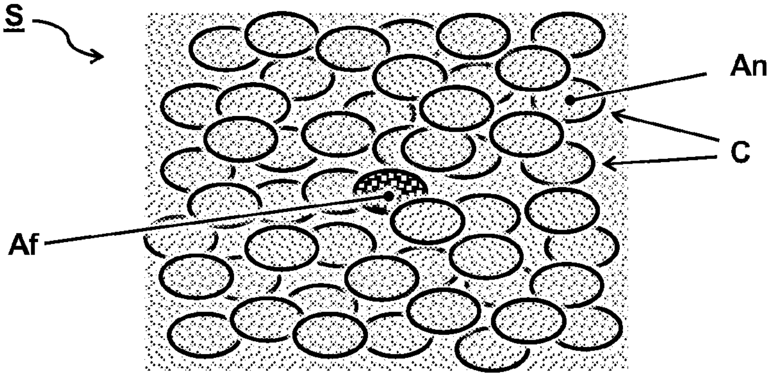
FIGS. 3A-3C illustrate isolating a phototagged target cell.
Figure 3B:
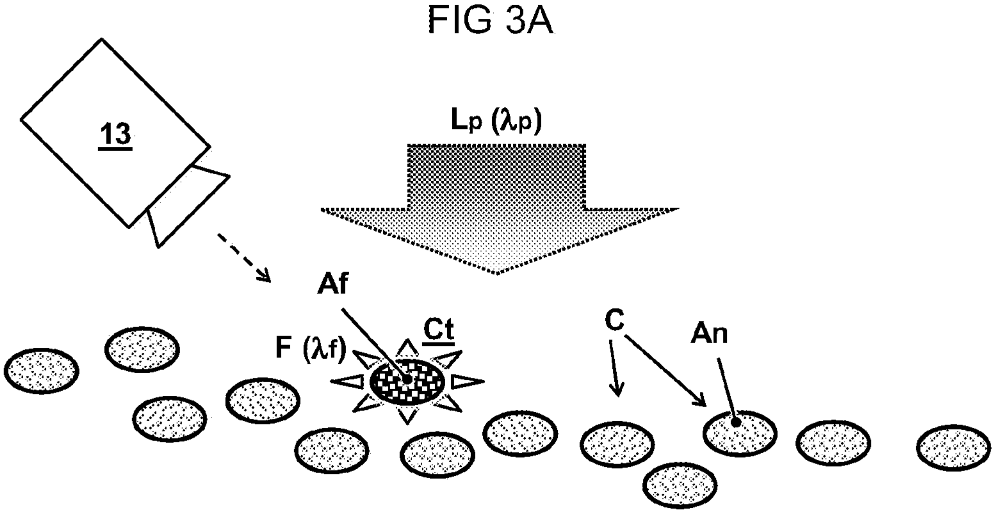
Figure 3C:
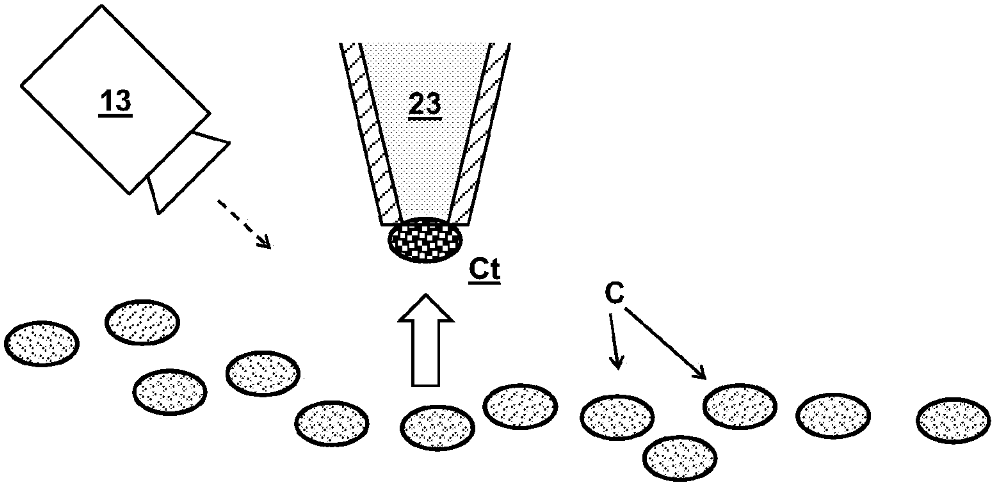

FIGS. 3A-3C illustrate isolating a phototagged target cell Ct. In some embodiments, isolating the target cell Ct comprises illuminating cells C from the sample S with probe light Lp. In other or further embodiments, the fluorescence response F of the illuminated cells C is measured. In other or further embodiments, the target cell Ct is isolated based on a difference in the fluorescence response F of the target cell Ct compared to other cells C in the sample S.

Fluorescence is generally understood as a form of luminescence. Typically the fluorescence response F may manifest as the emission of light by a substance (here: the activated phototagging agent Af) that has absorbed light or other electromagnetic radiation (probe light Lp). Typically, the emitted light corresponding to the fluorescence response F has a longer wavelength λf, and therefore lower energy, than a wavelength λp of the absorbed radiation, e.g. probe light Lp.

In some embodiments, a relative intensity of the fluorescence response F is used to distinguish the activated phototagging agent Af from the non-activated phototagging agent An. In other or further embodiments, the fluorescence wavelength λf of the fluorescence response F is used to distinguish the activated phototagging agent Af from the non-activated phototagging agent An. For example, the fluorescence wavelength λf may be in a distinct wavelength range from other light, e.g. other fluorescent molecules in the sample. Of course also combinations are possible wherein both wavelength and intensity are used to distinguish and isolate the cells after phototagging.

In some embodiments, the cells comprise a fluorescent compound in addition to the phototagging agent An. This may allow relatively easy imaging of the cells, e.g. using a fluorescence microscope, before and after the phototagging. This further compound preferably has a distinct fluorescence wavelength compared to the activated phototagging agent Af. For example, the cells may comprise both a molecule such as GFP (which emits a green fluorescent response); and a caged rhodamine-based phototagging agent (which emits a red fluorescent response, but only when uncaged or photoactivated by phototagging).

Figure 5:
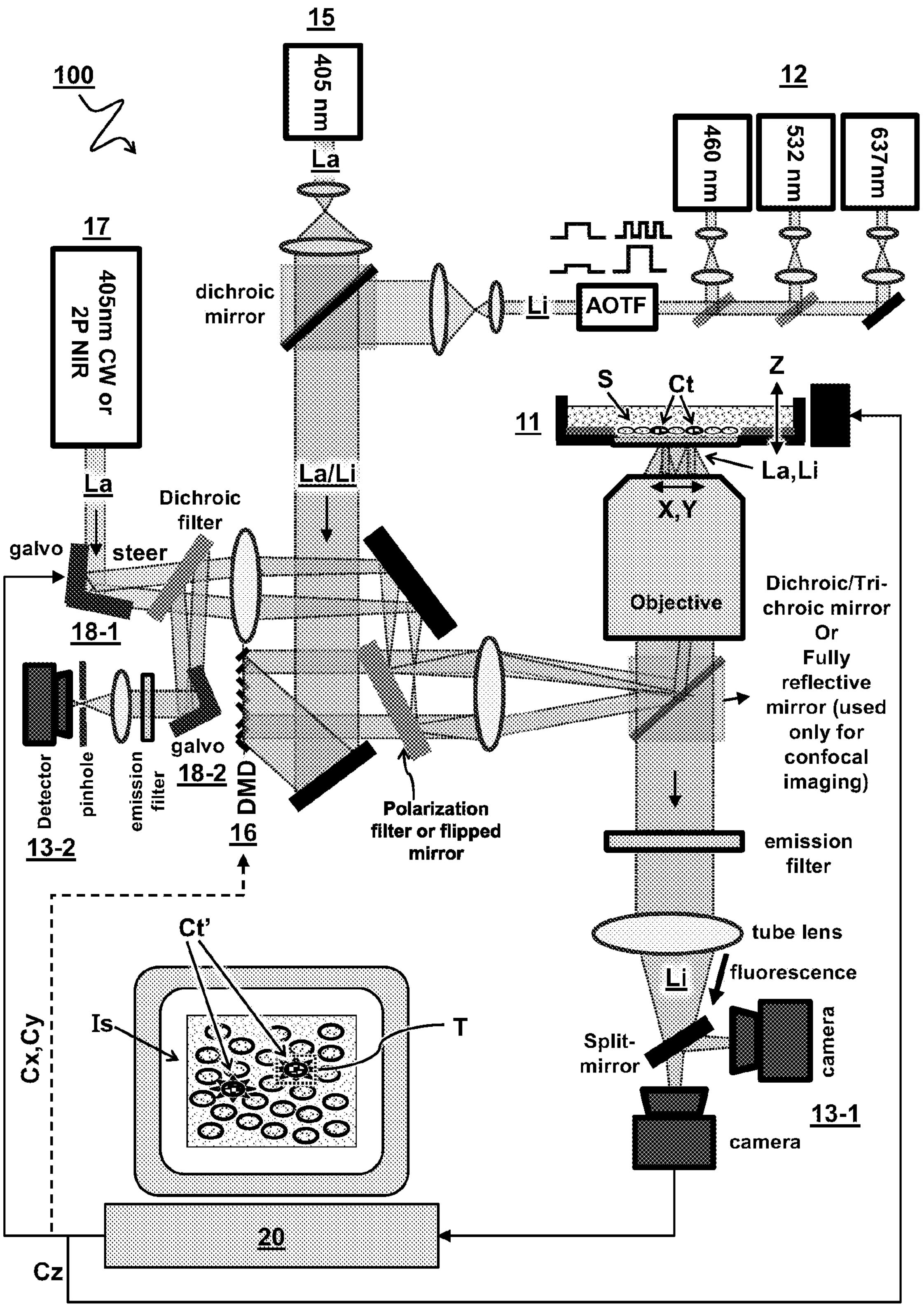

In some embodiments, the fluorescence response F is measured by a sensor or dual sensors 13, e.g. as shown in FIG. 5, (imaging) camera 13-1 or any other imaging or non-imaging light sensor 13-2. Alternatively, or additionally, the fluorescence response F can be observed by eye, e.g. via a microscope (not shown). In some embodiments, the target cell Ct is isolated by physically separating the target cell Ct from the rest of the sample S. For example, a pickup tool 23 can be used to pick up and isolate the target cell Ct. In a preferred embodiment, the isolating of target cells is automated, e.g. using a pickup tool 23 configured to automatically pick up one or more target cells Ct from a sample S based on their distinctive fluorescence response F measured by a sensor 13. Also other mechanisms for isolating cells can be envisaged. For example, the cells may be guided through a flow channel and sent in different directions depending on their fluorescence response F.

In some embodiments, the sample S is disintegrated, e.g. the sample is dissolved and/or the cells are separated from each other. This can make it easier to isolate the target cell Ct, e.g. in a three dimensional sample. In some embodiments, the cells C of the sample S are spread out on a substrate. For example, the pickup tool 23 can be used to pick the cell from the substrate. Alternatively, the spreading is already sufficient and the isolating comprises identifying the target cell Ct among the other cells.

Figure 4:
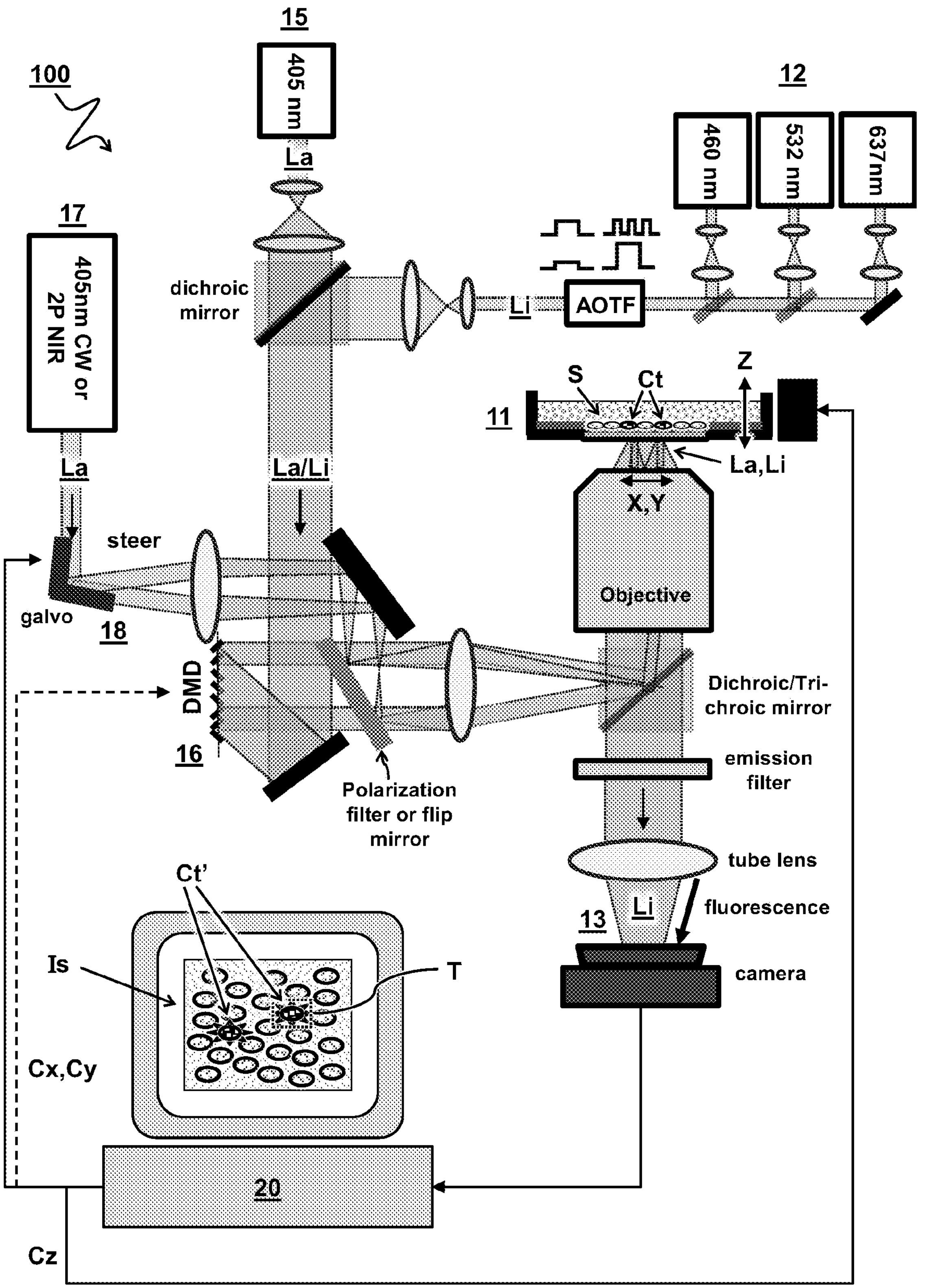
FIGS. 4 and 5 illustrates microscope systems for imaging and phototagging cells in a sample.

FIGS. 4 and 5 illustrate respective embodiments of a microscope system 100 for imaging and phototagging samples. In a preferred embodiment, the microscope system 100 is configured to perform the methods as described herein. In some embodiments, a sample holder 11 is configured to hold a sample S with cells C containing a phototagging agent An. In other or further embodiments, one or more image light sources 12 (or 17) are configured to illuminate the sample with imaging light Li. In other or further embodiments, at least one light detector (e.g. 13 in FIG. 4; 13-1, 13-2 in FIG. 5) configured to detect a sample image Is of the illuminated sample S for spatially resolving the cells C. In other or further embodiments, one or more photo-activation light sources 15, 17 configured to generate photo-activating light La for activating the phototagging agent to change its fluorescence response F.

In a preferred embodiment, a controller 20 configured to determine a target selection T of an imaged target cell Ct' based on the sample image Is, and determine target coordinates Cx, Cy of a corresponding target cell Ct in the sample S based on the target selection T. In other or further preferred embodiments, beam patterning and/or steering optics 16, 18 are configured to receive the target coordinates Cx, Cy of the target cell Ct, and selectively direct the photo-activating light La to irradiate a target location X, Y of the target cell Ct in the sample S based on the target coordinates Cx, Cy.

In one embodiment, target coordinates Cx, Cy, Cz of the target cell Ct in the sample S are determined based its identification in the imaging. For example, the image comprises a two or three dimensional mapping of cells in the sample. Positions of the cells in the image may thus be correlated (mapped) to their actual positions in the sample. Accordingly, the position of a cell selected on the basis of the imaging may be used to determine its location in the sample and the photo-activating light La can be selectively directed to the target location St. For example, a combined optical system can be used for both imaging and phototagging the cells, as described herein. The system may thus be calibrated to direct a position of the photo-activating light La to an imaged (target) position St in the sample S.

In some embodiments, at least one of the photo-activation light sources comprises a pulsed laser 17 which is focused at a specific location inside the sample S for photo-activating the phototagging agent An by two-photon absorption. For example, lenses or mirrors can be used to focus the beam. As explained before with reference to FIG. 2B, focused laser pulses may allow to activate phototagging agent at a specific depth in the sample using two-photon absorption which is limited to the focal region where the light intensity can be relatively high. In a preferred embodiment, the sample holder 11 comprises a moveable stage configured to vary a coordinate Z of the laser focus in the sample along an optical axis of the microscope based on at least one of the target coordinates Cz of the target cell Ct. Alternatively, or additionally, a depth of the focal position may be varied, e.g. by adjusting the lenses.

In some embodiments, the system comprises a light patterning device 16 in a light path between one or more continuous wave lasers or LED (light emitting diode) 12, 15 and the sample holder for patterning the photo-activating light La and/or imaging light Li onto the sample S. In other or further embodiments, the light patterning device 16 is arranged in a light path between at least one of the photo-activation light sources 15 and the sample holder 11 for selectively applying the photo-activating light La onto the selected target cell Ct of an essentially two-dimensional sample S.

In a preferred embodiment, the system is configured for wide-field imaging of the sample. Most preferably, the microscope offers the ability to image with both high resolution and large FOV, both with one photon and two photon excitation, and in both two-dimensional (2D) and three-dimensional (3D) samples. By imaging a large part of the sample at once, multiple cells can be simultaneously imaged and tracked. In some embodiments, the light patterning device 16 is arranged in a light path between at least one of the image light sources 12 and the sample holder 11 for applying a pattern of the imaging light Li.

In a preferred embodiment, the system is configured for (fast) volumetric imaging reconstruction of 3D samples using wide-field or scanning imaging methods allowing planar section, including but not limited to scanning two-photon microscopy, structured illumination microscopy or Hadamard imaging. In general, the system can be configured for 2D or 3D image reconstruction using any illumination method and image reconstruction method that can be used to create imaging contrast, including but not limited to white-light imaging, phase-contrast imaging, bright-field imaging, dark-field imaging, wide-field fluorescence imaging or scanning confocal imaging.

In some embodiments, a three dimensional image or map of the sample S is recorded or registered, e.g. using 3D-structured illumination microscopy, multi-photon imaging or any other suitable technique such as confocal microscopy. Also other or further devices may be arranged in a light path between one or more light of the image light sources 12 and the sample holder 11. For example, an acousto-optic tunable filter (AOTF) can be used to rapidly and dynamically select a specific wavelength from a broadband or multi-line laser source, as shown. For example, different (fluorescence) images of the sample S may be taken by illuminating at different wavelengths. Multi-line light sources can include any desired wavelengths of light, not limited to the shown 460, 532 or 637 nm.

In some embodiments, e.g. as illustrated in FIG. 5, imaging of the sample can be done either in widefield or confocal configuration by switching the dichroic/trichroic filter in the emission path to a fully reflective mirror. As will be appreciated, advantages of the present disclosed microscope systems may include imaging a large quantity of cells (e.g. hundreds thousands of or ~millions of cells) with high spatial (sub-cellular; <micrometer) and temporal (microseconds, milliseconds, seconds or minutes depending on users' preference) resolution. To facilitate capturing such a large quantity of cells without losing temporal resolution, dual detectors (e.g. cameras 13-1) can be implemented in some embodiments, which can simultaneously capture dual fields of view. To facilitate imaging finite sub-cellular structures that are below the spatial resolution of the microscope's standard operation, an additional moiety can be implemented in the setup and can be chosen if needed, e.g. switching the dichroic/trichroic mirror at the emission path to a fully reflective mirror so that confocal imaging can be performed. Confocal imaging implemented in the setup can yield two to several folds of improvement in terms of spatial resolution (e.g. from 0.8 micrometer to 0.4 micrometer with a two fold improvement).

In some embodiments such as shown in FIG. 5, the imaging setup may include one or more sets of galvo mirrors (e.g. 18-2). For example, this can be used for confocal imaging instead of, or in addition to, wide-field imaging. Also other or further components can be included in the imaging path, e.g. a pinhole and/or emission filter as shown in FIG. 5. While the present system shows a second galvo mirror 18-2, it can also be envisaged to (re)use the same galvo mirror 18-1 for the same or similar purpose in other embodiments (not shown).

Figure 6:
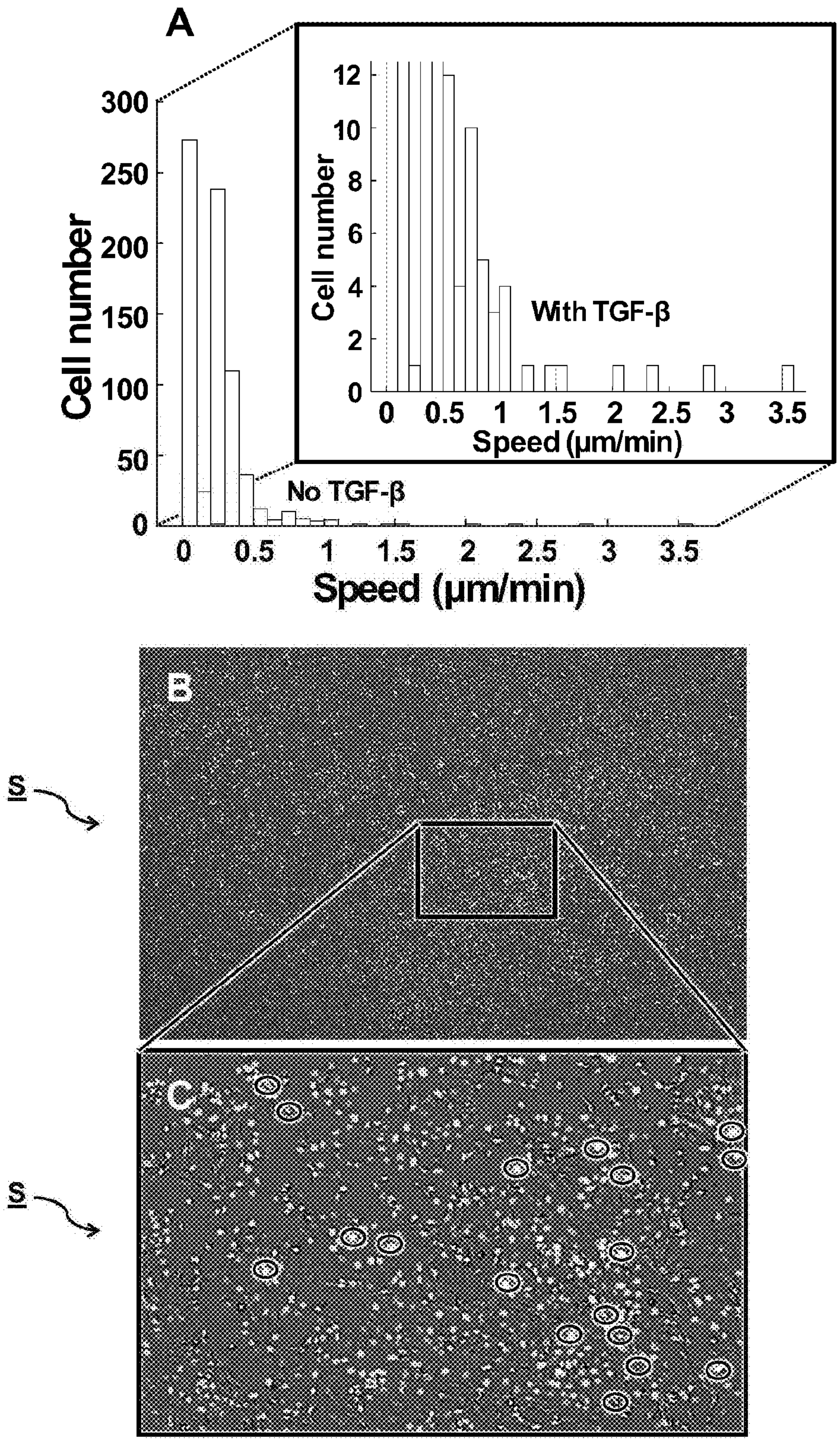
FIG. 6 illustrates automatic phototagging of cells based on corresponding images.

FIG. 6 illustrates automatic phototagging of cells based on corresponding images. The top (A) shows a histogram of migratory speed of the top 1% fastest MCF10A-GFP cells treated without or with TGF-β. The middle image (B) illustrates MCF10A-GFP cells treated with TGF-β for two days. After analyzing individual cells' migratory speed, the top 1% of fast moving cells red were identified and selected by Phototagging. This image also demonstrates the relatively large field of view with high spatial resolution that can be obtained by the instrument described herein. The bottom image (C) illustrates zoomed-in image of B. In this image, the fluorescence response of phototagged cells is indicated by circles (red light) while the other cells only show their default fluorescence caused by the GFP (green light). This image demonstrates single cell selection based on functional data (fast migration) in 2D cell cultures using phototagging In general, the images illustrate that advantageous application of the present teachings may be embodied as methods or systems for automatic phototagging of cells based on any image analysis of a sample. In the embodiment shown, migratory speed was used as criterion for the automatic phototagging of subset of cells. Additionally, or alternatively also other criteria can be defined based on one or more recorded images of the sample. For example, the phototagging may be based on one or more of a size, shape, or any other characteristic of the cells such a gene expression, or their interaction, in one or more recorded images of the sample.

With reference e.g. to FIG. 4, some embodiments comprise analyzing one or more sample images Is to automatically identify and/or track one or more target cells Ct based on a predetermined criterion. Other or further embodiments comprise controlling the beam patterning and/or steering optics 16, 18 to direct the photo-activating light La to irradiate one or more target locations in the sample corresponding to the one or more target cells Ct. In one embodiment, the methods and systems described herein can be applied to downstream single cell whole genome, transcriptome, epigenome and proteome analysis. For example, the system can identify and isolate (especially sparse) target cells, which can be further profiled to identify sparsely expressed yet significant genes, that cannot be identified using current single cell RNA-seq methods.

Figure 7:
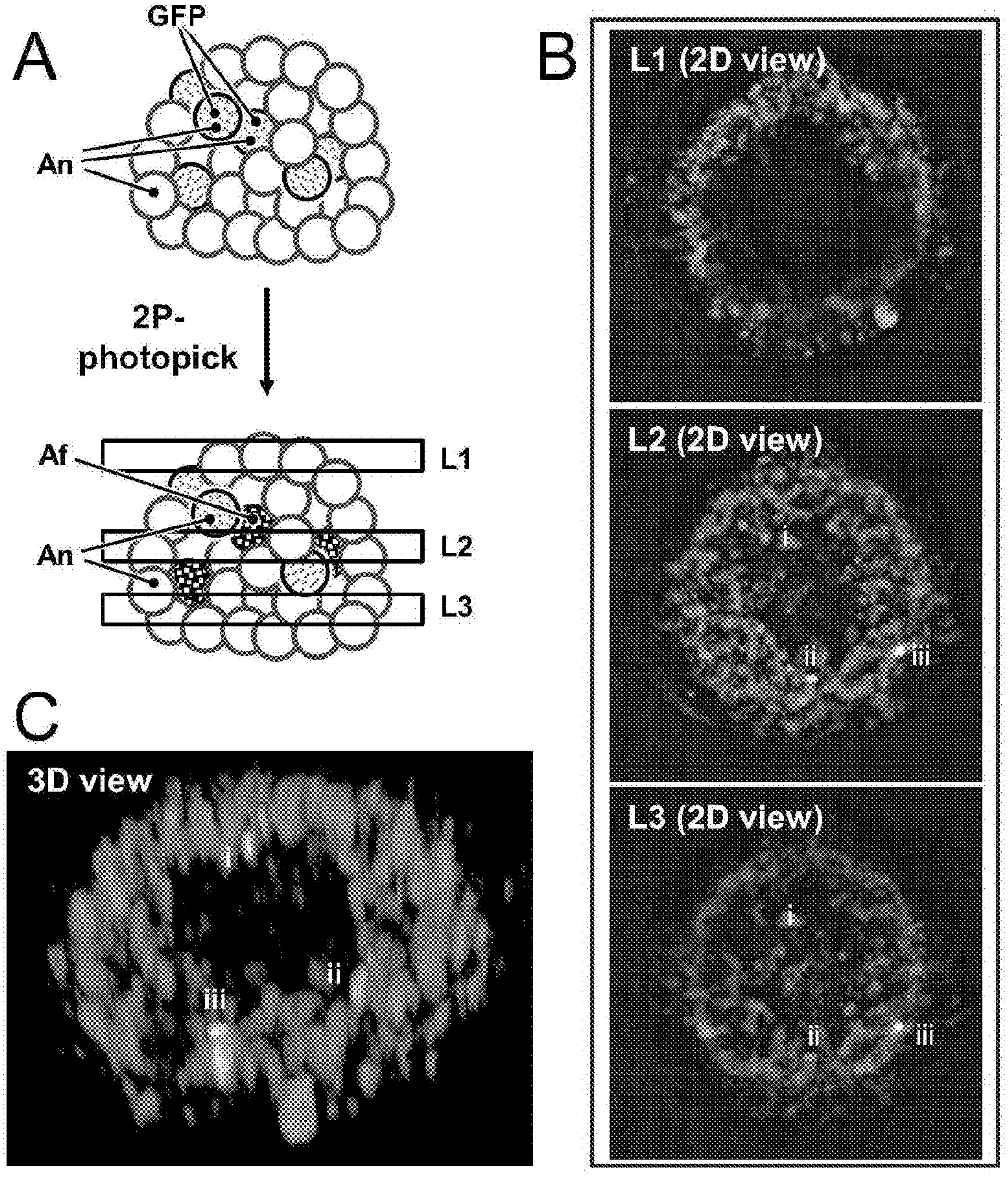
FIG. 7 illustrates single cell selection from 3D samples using two-photon (2P)-phototagging.

FIG. 7 illustrates single cell selection from 3D samples using two-photon (2P)-phototagging. Inset "A" illustrates a 3D tumorsphere a mixture of MCF10A-GFP/MCF10A cells used in insets "B" and "C". There were 6 GFP-labeled cells in the tumorsphere, three of which were 2P-phototagged (indicated by darker color). Inset "B" shows three layers (L1-L3) of a 2D view of the tumorsphere. layer "L2" shows three MCF10A-GFP cells were 2P-phototagged (i-iii), two of which were again seen in the layer L3 (ii, iii). Inset "C" shows a 3D view of the tumorsphere. i-iii are three 2P-phototagged MCF10A-GFP cells.

Further aspects will now be described relating to a preferred chemical compound that can be particularly suitable for use as a phototagging agent in the method or system as described herein.

In a preferred embodiment, the chemical compound comprises a caged fluorophore moiety. Caged fluorophores (also referred to a photoactivatable fluorophores or caged dyes) are weakly or non-fluorescent molecules that can be photochemically converted to fluorescent dyes when excited at the appropriate wavelengths. Caged fluorophores as such are known in the art, see e.g. Li et al. Photochemical and Photobiological Sciences 11 (2012) 460-471 and Raymo F. M. ISRN Physical Chemistry (2012), doi: 10.5402/2012/619251. Typically, caged fluorophores stay in their non-fluorescent state by the incorporation of a photochemical labile group or caged moiety such as a nitrophenyl derivative. For example, the photosensitive caged moiety can be cleaved off by irradiation with near-UV light, thereby rendering the fluorescence of the dye.

A potential drawback of known caged fluorophores is that the wavelength for photoactivation is typically relatively low, e.g. an ultraviolet wavelength range. For example, the known caged fluorophores provide the most efficient performance (uncaging) using illumination at or around a wavelength of 365 nm. Such wavelength could potentially be harmful for some cells. While this may be acceptable in some cases, in other cases these known caged fluorophores may be less preferred for some embodiments of the present application of cell isolation, as described herein.

The present inventors surprisingly found a chemical compound that does not suffer from the above-described drawback of known caged fluorophores, which compound allows a better customization of the activation wavelength. It was surprisingly found that if the compound comprises a caged fluorophore conjugated to a photosensitizer moiety, the compound can be uncaged by irradiating the compound with light of a wavelength for which the caged fluorophore moiety is essentially insensitive but which can efficiently be absorbed by the photosensitizer to cause the uncaging. As such, for example, by conjugating the caged fluorophore moiety to a photosensitizer moiety that can efficiently absorb light of a wavelength >400 nm, efficient uncaging can be achieved even though the caged fluorophore moiety itself is essentially insensitive to the light of a wavelength >400 nm. By this approach, known caged fluorophores can be relatively facile be adjusted to be particular suitable for the method or system as described herein.

Photosensitizers are understood as compounds that can facilitate the photocleavage of the protecting group (or caged moiety) from the caged fluorophores so that the uncaging processing can be significantly improved. Photosensitizers absorb light energy upon irradiation. The energy may (or charge) may be transferred to the nearby photolabile group (caged moiety) in the caged fluorophores, to activate the fluorophores. Photosensitizers are commonly used in reactions such as photopolymerization, photocrosslinking, and photodegradation. An example of a suitable photosensitizer is for instance thioxanthone, which as such is known for its use in DNA-chip synthesis. Wöll D. et al. Angew. Chem. Int. Ed. 45 (2006), 2975-2978.

Figure 12:
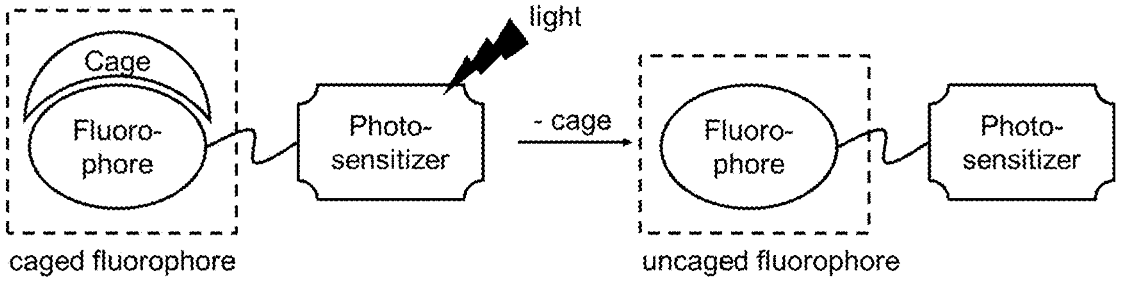
FIG. 12 illustrates the chemical compound and the uncaging proceeding schematically.

Without wishing to be bound by theory, the chemical compound and the uncaging schematically proceeds as illustrated in FIG. 12. In a preferred embodiment, the photosensitizer moiety absorbs light of a wavelength from 360 nm-420 nm while the caged fluorophore moiety is essentially insensitive to light of a wavelength >400 nm. This typically means that the absorption coefficient of the photosensitizer as a wavelength of higher than 400 nm is more than 10 times, preferably more than 40 times as high as the absorption coefficient of the caged fluorophore moiety at the same wavelength. For example, a UV-Vis absorption spectrum shows that the caged rhodamine without thioxanthone doesn't have absorption >400 nm, whereas the caged rhodamine with thioxanthone has absorption >400 nm (drops at ~420 nm).

In principle, any caged fluorophores can be used for conjugation to the photosensitizer. Examples of particularly suitable caged fluorophore are those based on fluorone-based fluorophores, coumarin-based fluorophores, cyanine-based fluorophores and DCDHF-based fluorophores. Flourones include fluorescein-, erythrosine- and rhodamine-based fluorophores. Specific examples of rhodamine-based fluorophores are rhodamine 123, rhodamine B and rhodamine 6G. Coumarin-based fluorophores are also well known in the art and include derivatives of 7-hydroxycoumarin and the like (e.g. 7-hydroxycoumarin-3-carboxylic acid, 6,8-difluoro-7-hydroxy-4-methylcoumarin (DiFMU), and 7-amino-4-methylcoumarin). DCDHF-based fluorophores are based on 2-dicyanomethylene-3-cyano-2,5-dihydrofuran (DCDHF, see e.g. Lord et al., ChemPhysChem 10 (2009) 55-65).

Photosensitizer moieties based on thioxanthones give particular good results, but other photosensitizers such as thiopyrylium (e.g. 2,4,6(4-methoxyphenyl) thiopyrylium (TP)), camphorquinone, eosin (e.g. eosin-Y) and acridinedione derivatives (e.g. AD-1 and/or AD-2) may also suitably be used in this aspect. Structures of photosensitizers on which the photosensitizer moiety can be based are provided in Scheme 1.

Scheme 1

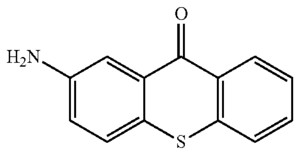

amino-thioxanthone

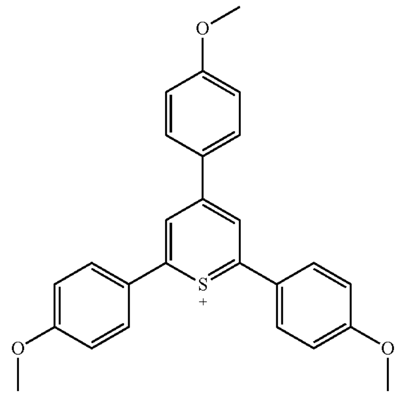

2,4,6(4-methoxyphenyl)-thiopyrylium (TP)

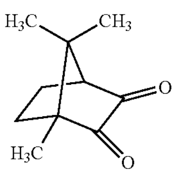

Camphorquinone

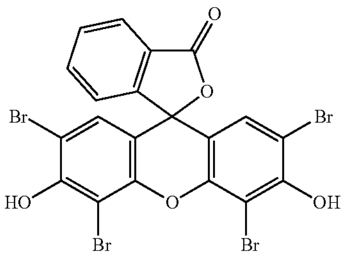

Eosin-Y

AD-1

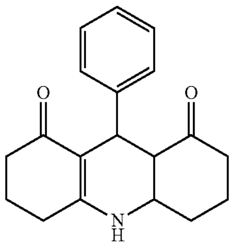

AD-2

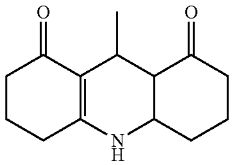

Preferably, the conjugation, attachment or molecular connection of the photosensitizer moiety to the caged fluorophore moiety is done at a position of the caged fluorophore moiety that is already a suitable substituent or anchoring point. Example thereof include carboxylic acid groups, N-Hydroxysuccinimide, amino groups, hydroxyl groups and the like. For instance, the caged fluorophore moiety may comprise a carboxylic acid functionality that is reacted with a photosensitizer having an amine functionality. Suitable derivative of the compounds in Scheme 1 are typically readily available. Optionally, a linker group may be used to conjugate the caged fluorophore moiety and the photosensitizer moiety.

Specific examples of the chemical compound include those having a structure according to any one of structures I, II, III or IV

I

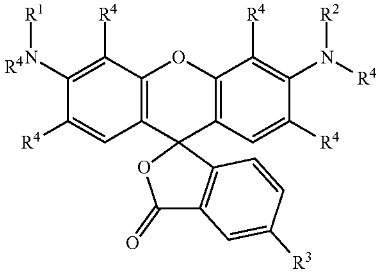

II

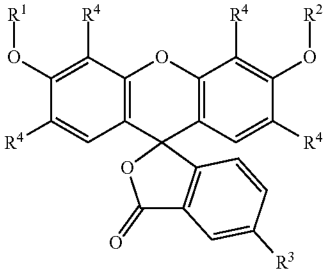

III

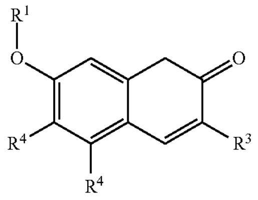

IV

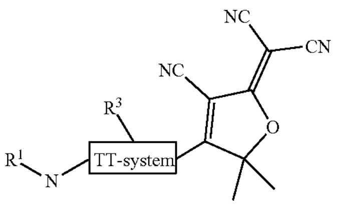

wherein the core of said structure represents the fluorophore moiety, $R^1$ and $R^2$ individually represent a caged moiety and individually comprise a photo-liable group, preferably a nitrobenzyl or nitrophenyl group; $R^3$ represents the photosensitizer moiety, and each $R^4$ is individually selected from the group consisting of H, halide, $C_1$-$C_6$-alkyl, $C_1$-$C_6$-alkoxy, $C_1$-$C_6$-alkylenes and $C_1$-$C_6$-alkoxylenes.

With the core of said structures is meant the moiety including all the atoms shown for the structures, excluding the $R^1$, $R^2$, $R^3$ and $R^4$ substituents. Thus, structure I is based on a rhodamine core, structure II on a fluorescein, structure III on a coumarin core, and structure IV on a DCDHF core. Of structure IV, the n-system represents a moiety that conjugates the $R^1N$ donor group and the 2-dicyanomethylene-3-cyano-2,5-dihydrofuran (DCDHF) acceptor group, as described in Lord et al., ChemPhysChem 10 (2009) 55-65.

In preferred embodiments, some particular $R^4$ substituents are H, as illustrated by structures Ia, IIa and IIIa, wherein $R^1$, $R^2$, $R^3$ and $R^4$ are as defined above for structures I, II and III.

Ia

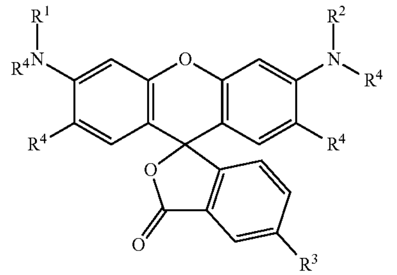

IIa

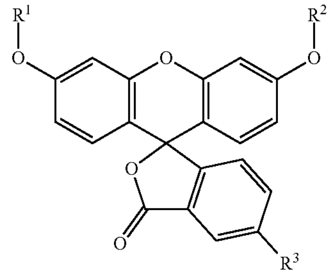

IIIa

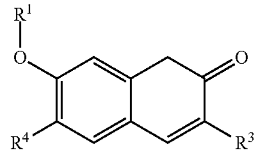

More preferred embodiments of structures I and IV are Ib and IVb, wherein $R^1$, $R^2$, $R^3$ and $R^4$ are as defined above for structures I and IV.

Ib

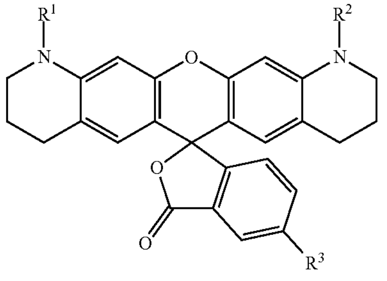

-continued

IVb

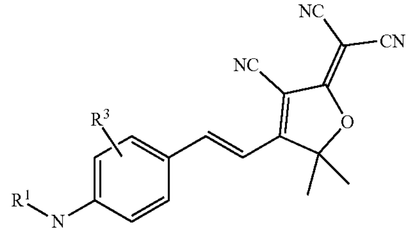

The photosensitizer moiety $R^3$ can be based on those photosensitizers described herein above (e.g. those in Scheme 1). These photosensitizers can be acquired and conjugated to the core of said structure using chemical reactions such as amide bond formation, esterification, etherification and the like.

Particularly preferred embodiments of the above structures are those wherein $R^3$ comprises a group of the structure V, preferably Va or Vb, wherein n is an integer >0, preferably 2. The $—NH(CH_2)_nC(O)—$ group can herein be regarded as said linker.

V

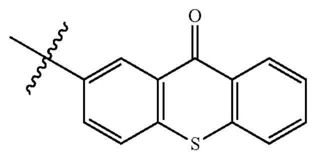

Va

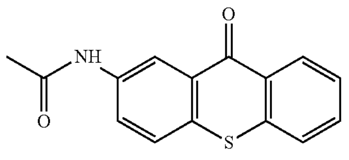

Vb

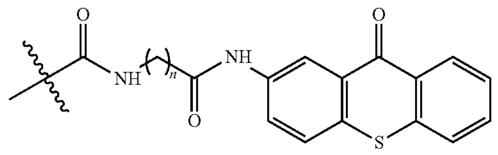

In a most preferred embodiment, the chemical compound according to any of the preceding claims, selected from the group consisting of chemical compounds A, B and C.

Chemical compound A

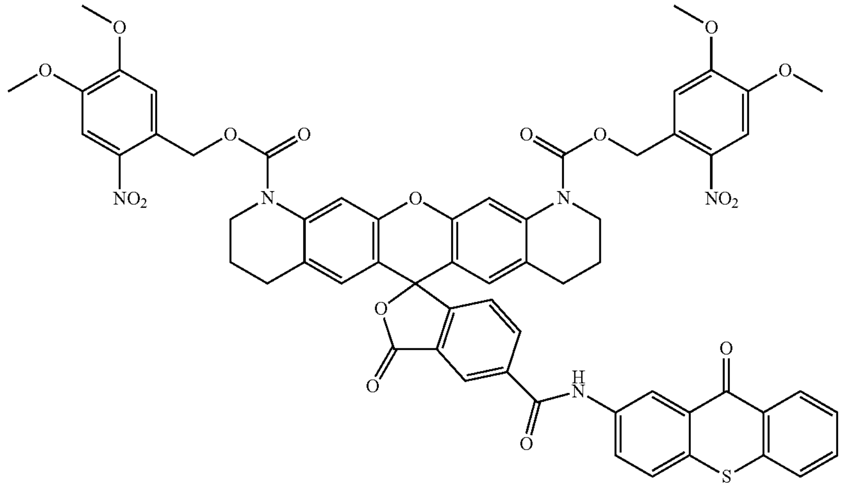

Chemical compound B

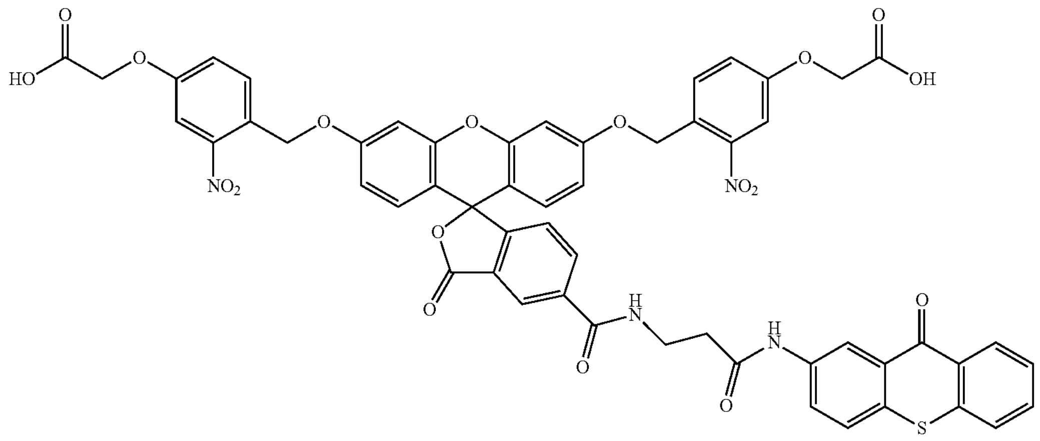

Chemical compound C

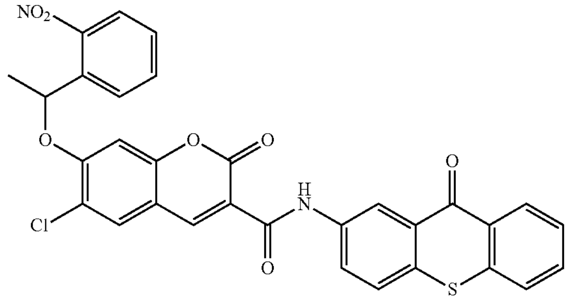

Without wishing to be bound by theory, the inventors believe that upon radiation of the chemical compound with a wavelength range of 365 nm to 410 nm, the uncaging of the rhodamine-based chemical compound proceeds by absorption of the majority of the light energy by the thio-xanthone and transfer of at least part of said energy to the said caged fluorophore, such that uncaging is triggered, as is illustrated in Scheme 2.

Scheme 2

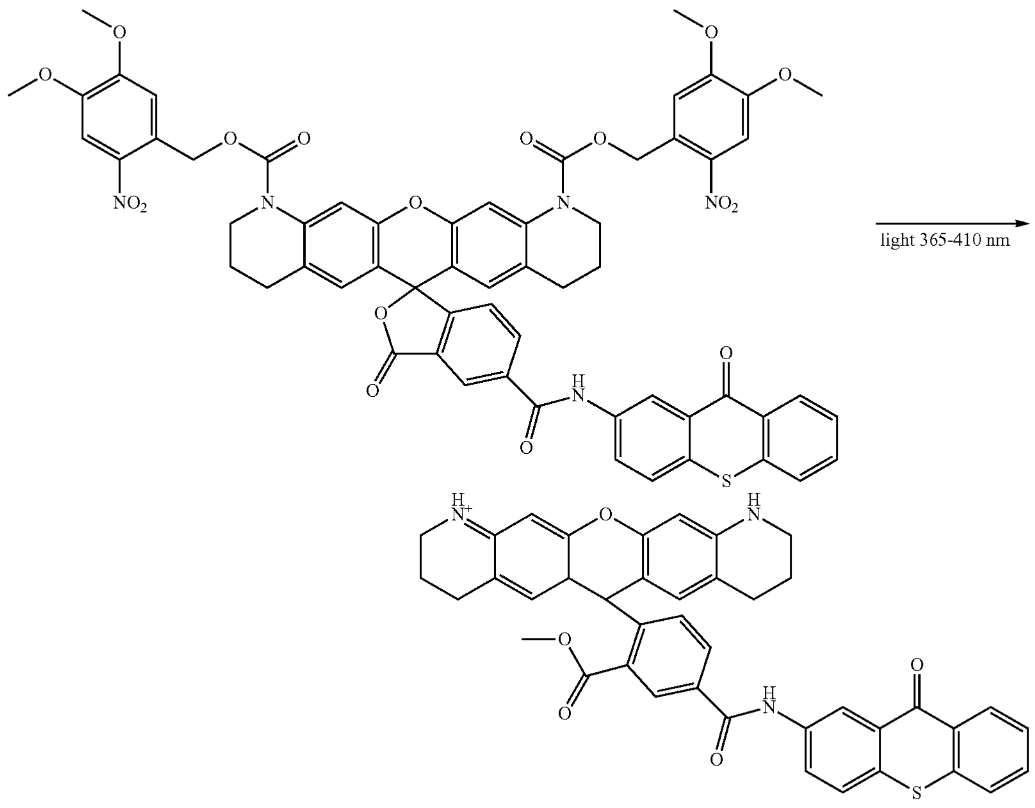

Figure 8:
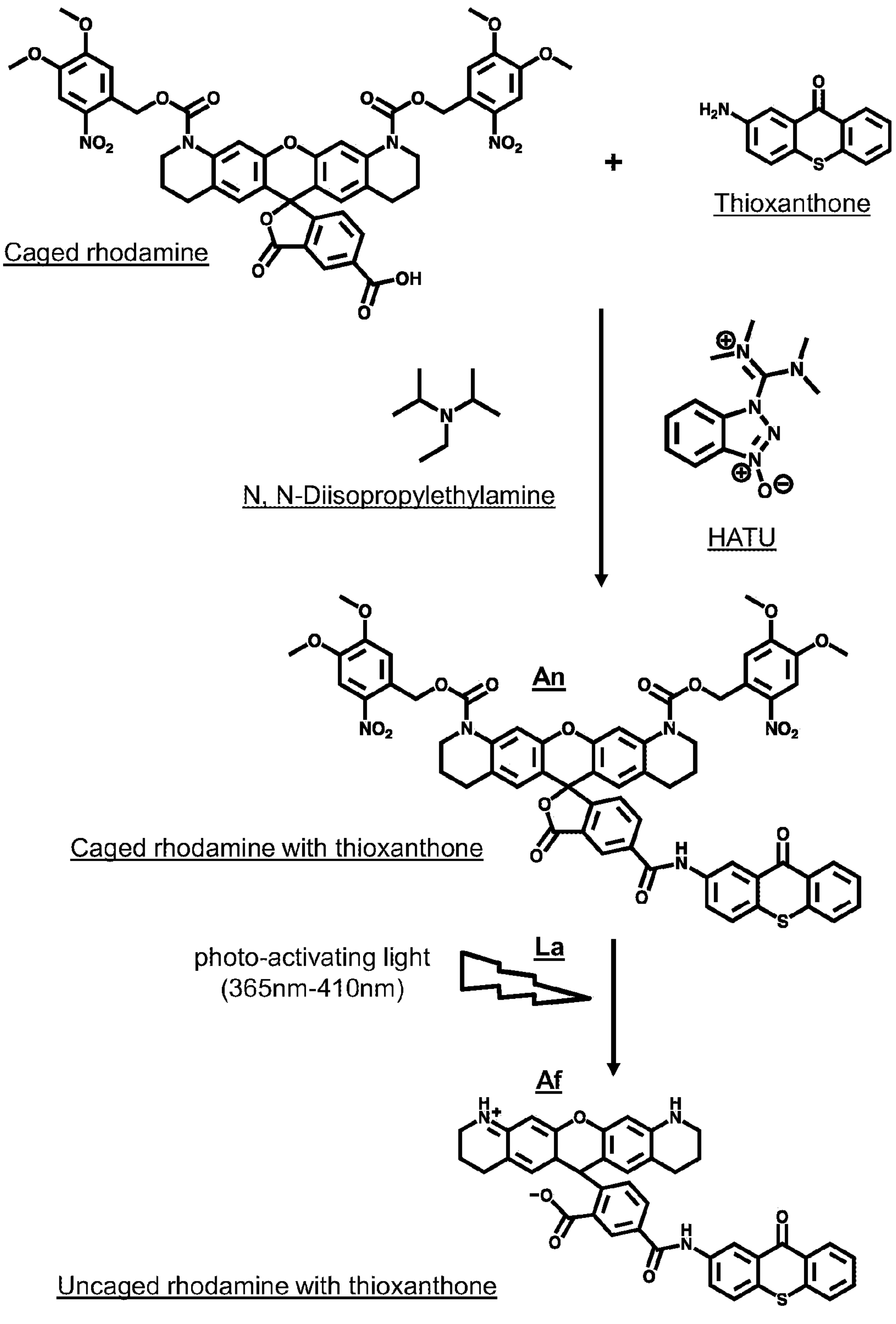
FIG. 8 illustrates an embodiment for synthesis of a phototagging agent and its uncaging process by photo-activating light to produce a corresponding fluorescent agent.

FIG. 8 illustrates an embodiment for synthesis of a phototagging agent An and its uncaging process by photo-activating light La to produce a corresponding fluorescent agent Af. In this embodiment, the phototagging agent An is a rhodamine based compound with two nitrophenyl cages and thioxanthone as a photosensitizer.

Figure 9:
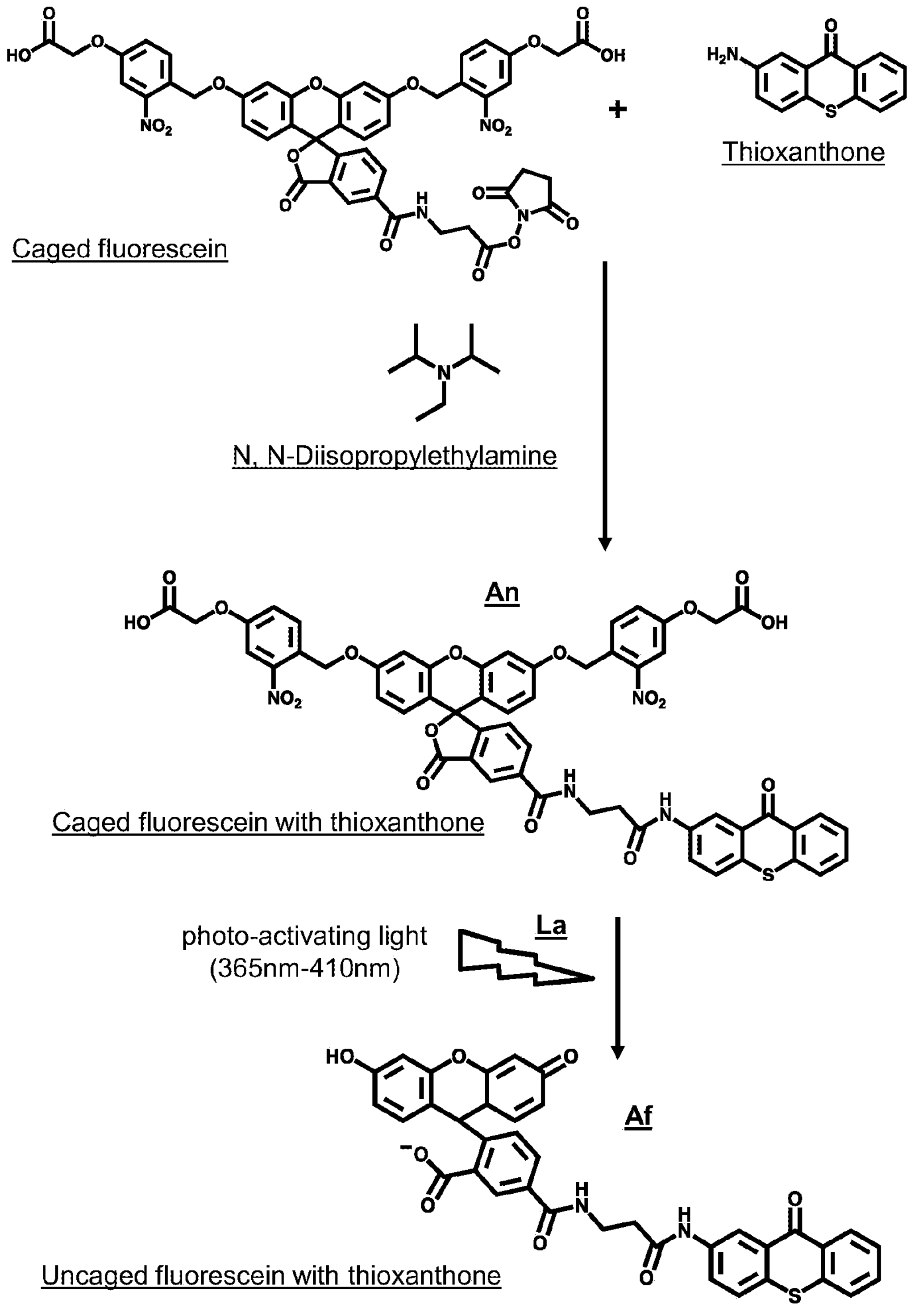
FIG. 9 illustrates another phototagging agent and corresponding processes.

FIG. 9 illustrates a similar embodiment for another phototagging agent An and corresponding processes. In this embodiment, the phototagging agent An is a fluorescein based compound.

Figure 10A:
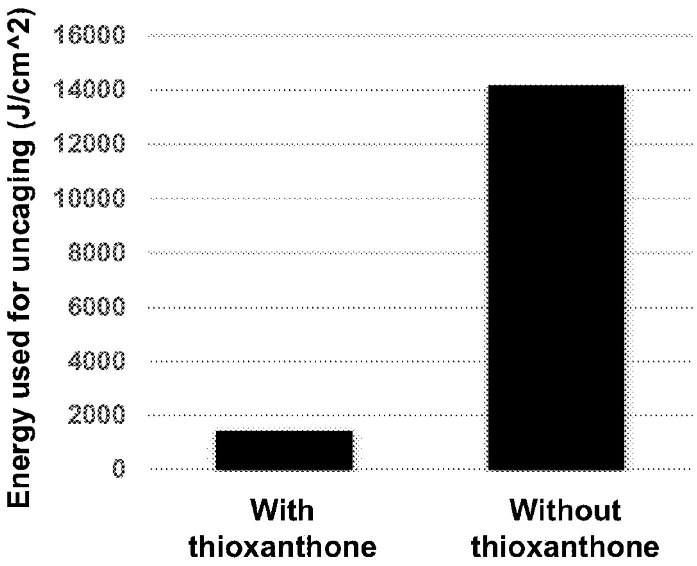
FIG. 10A illustrates a graph of uncaging efficiency of caged rhodamine conjugated with or without photosensitizer (thioxanthone)

FIG. 10A illustrates a graph of uncaging efficiency of caged rhodamine with or without photosensitizer (thioxanthone). As shown, the uncaging efficiency (or energy needed) can be drastically improved by the addition of a photosensitizer, e.g. improved by more than a factor two, five, or even ten (as shown here).

Figure 10B:
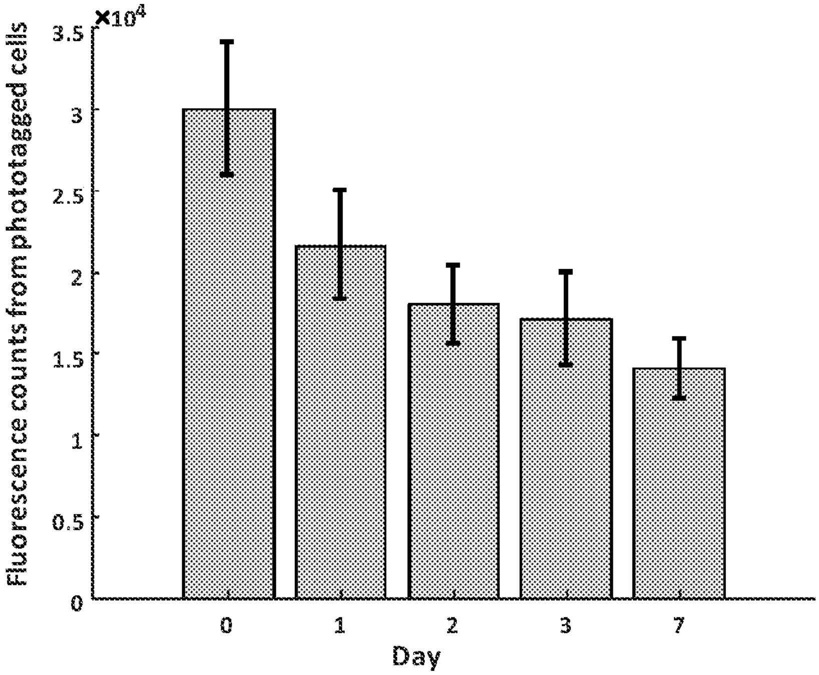
FIG. 10B shows a graph of average value of fluorescence counts over a time period from several phototagged cells.

FIG. 10B shows a graph of average value of fluorescence counts over a time period from several phototagged cells. The graph illustrates that, upon uncaging, the uncaged phototagging agent (with charge) can remain inside the cells for a long time e.g. seven days. In one embodiment, the hydrophobicity of the phototagging agent makes it cell permeable. In some embodiments, a hydrophobic property of a compound may be demonstrated by its ability to be dissolved in an organic solvent like DMSO, but not in aqueous solution (e.g. water). For example, the solubility of a hydrophobic or cell-permeable compound is at least twice as high in DMSO than it is in water, or at least five or ten times as high. One example for measuring the hydrophobicity may be as follows: 10 mg of the compound could be dissolved in 1 mL DMSO organic solvent 8.8 mM, but not in aqueous solutions at room temperature. While diluting to ~50 uM, the compound could be dissolved in aqueous solutions at room temperature.

Figure 11A:
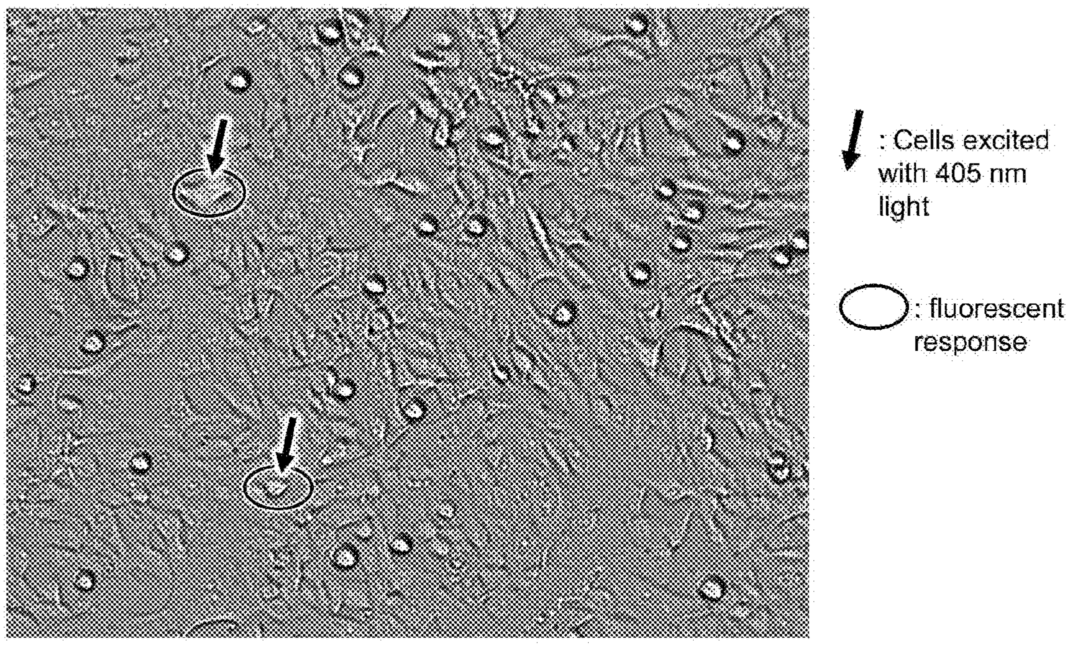
FIGS. 11A and 11B illustrate images of cells incubated with a phototagging agent conjugated with and without photosensitizer, respectively.
Figure 11B:
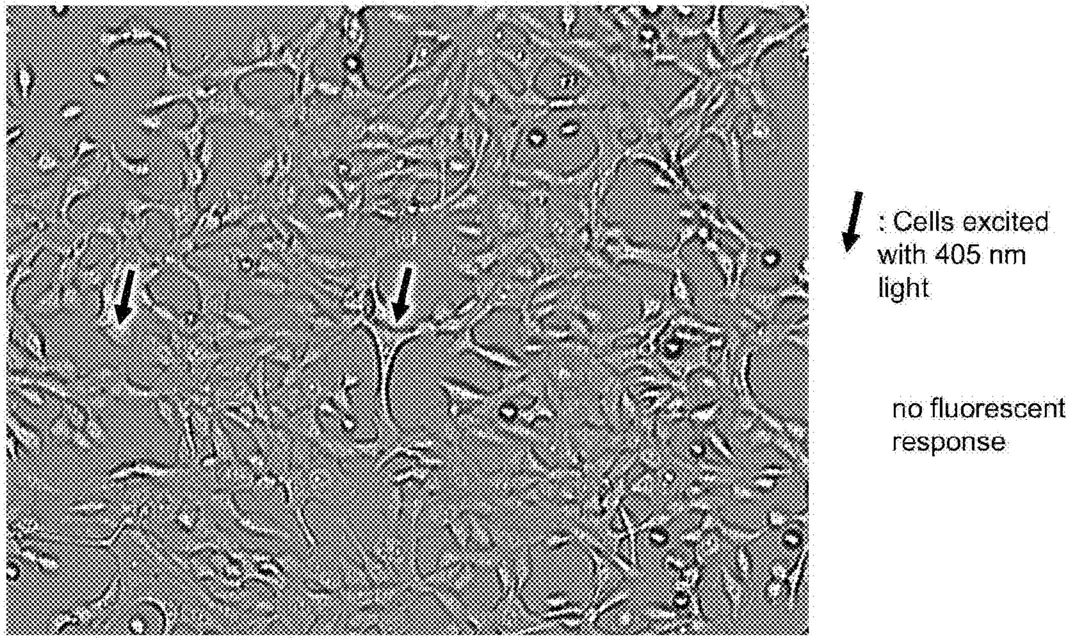

FIGS. 11A and 11B illustrate images of cells incubated with a phototagging agent, with and without photosensitizer, respectively. The top image shows cells incubated with 15 μM caged rhodamine conjugated with thioxanthone; and the bottom image shows cells incubated with 15 μM caged rhodamine without thioxanthone. The arrows in both images indicate where cells were activated, in both cases with 405 nm (1000 J/cm^2) light. In the top image, a fluorescent response F could be measured from the irradiated (activated) cells (normally measured as red fluorescent light, in this gray image indicated by the circles). In the bottom image, no fluorescent response was measured at the irradiated location, or anywhere else.

In a preferred embodiment, uncaging efficiency of the phototagging agent including the photosensitizer may be increased by at least a factor two, three, five, ten, or more, e.g. as shown in the comparative example of FIG. 10A. For example, uncaging efficiency is determined by a relative decrease in the energy or intensity of light needed to uncage the phototagging agent. For example, a wavelength at which the amount of energy or intensity is compared is more than four hundred nanometer, e.g. 405 nm as shown in the comparative example of FIGS. 11A and 11B.

Some aspects of the present disclosure can be illustrated by the following examples.

EXAMPLE 1—PREPARATION OF CAGED RHODAMINE WITH THIOXANTHONE (CHEMICAL COMPOUND A)

To a stirred solution of caged rhodamine (1 mole ratio; 0.0086 mmol) in dry DMSO (500 uL) was added thioxanthone (2 mole ratio; 0.0172 mmol), HBTU coupling agent (4 mole ratio; 0.0343 mmol) and trace N, N-Diisopropylethylamine (0.5 uL). The reaction was stirred overnight under a nitrogen atmosphere. The product was purified using HPLC (retention time: 23.1 min; RP-C18 column with a 30 min gradient of 50% to 100% ACN containing 0.1% TFA). MS: 1142.11 [M+H]+.

A similar synthesis scheme as shown in Example 1 can be also applied to the synthesis of compound B and C.

EXAMPLE 2—DETERMINATION OF UNCAGING EFFICIENCY OF CAGED RHODAMINE WITH OR WITHOUT THIOXANTHONE (CHEMICAL COMPOUND A)

The comparison is carried out by directly measuring uncaging efficiency in biological samples. The described experiment was conducted in mammalian cancer cell lines but can be generalized without loss of relevance to other mammalian cell types. The phototagging agent (caged rhodamine with thioxanthone) at 15 uM was incubated with MCF10A cells for 15 min. The caged moiety was then removed by irradiation with 405 nm CW light at 500-1500 J/cm^2. Whereas the caged moiety of caged rhodamine without thioxanthone could be only removed with 405 nm CW laser at ~15000 J/cm^2. The uncaged rhodamine in the cells was imaged by 532 nm excitation (200 mW/0.35 cm^2).

The results are depicted in FIG. 10A. it was found that uncaging of chemical compound A is more than ten times more efficient compared to the corresponding caged rhodamine without the photosensitizer thioxanthone (FIG. 10A). Upon 405 nm exposure (1000 J/cm^2), the phototagging agent inside of cells was photoactivated (arrows and circles in FIG. 10A). However, caged rhodamine without thioxanthone was not photoactivated under the same illumination condition (arrows in FIG. 11B).

EXAMPLE 3—CELL PERMEABILITY COMPOUND A

The cell permeability assay was conducted by directly measuring fluorescence of the phototagged cells and by monitoring the retention time of the activated dye inside of the phototagged cells. 15 uM of phototagging agent (caged rhodamine with thioxanthone) was incubated with the cells for 15 min. The unreacted agent was then rinsed away with PBS (phosphate buffered Saline). Next, the cells were illuminated with 405 nm light (1000 J/cm^2). After activation, fluorescence of photoactivated uncaged rhodamine was observed and imaged by 532 nm excitation (200 mW/0.35 cm^2). The photoactivated fluorescence could be observed until day 7 post-photoactivation, indicating that the uncaged phototagging agent (with charge) could stay inside of cells for 7 days (see FIG. 10B).

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A method for isolating cells, the method comprising providing a sample with cells containing a phototagging agent comprising a caged fluorophore moiety, optionally conjugated to a photosensitizer moiety;

imaging the sample to identify at least one target cell to be isolated;

selectively irradiating the identified target cell in the sample with photo-activating light for selectively activating the phototagging agent in the target cell to change its fluorescence response; and isolating the irradiated target cell from other cells in the sample based on a difference in its fluorescence response compared to non-activated phototagging agent in the other cells.

2. The method according to claim 1, wherein the sample is three dimensional sample with multiple layers of cells along a beam direction and the phototagging agent is activated by multi-photon absorption exclusively at a focal spot of the photo-activating light in a subset of one or more of the layers.

3. The method according to claim 1, wherein the phototagging agent comprises the photosensitizer moiety, and the photo-activating light is in a wavelength range above 360 nm to activate the photosensitizer moiety.

4. The method according to claim 1, wherein isolating the target cell comprises illuminating cells from the sample with probe light measuring a fluorescence response of the illuminated cells; and physically separating the target cell from other cells in the sample based on a difference in the fluorescence response of the target cell compared to the other cells.

5. The method according to claim 1, using a microscope system comprising a sample holder configured to hold the sample with cells containing the phototagging agent;

one or more image light sources configured to illuminate the sample with imaging light;

at least one light detector configured to detect a sample image of the illuminated sample for spatially resolving cells in the sample;

a controller configured to determine a target selection of an imaged target cell based on the sample image, and determine target coordinates of a corresponding target cell in the sample based on the target selection;

one or more photo-activation light sources configured to generate photo-activating light for activating the phototagging agent to change its fluorescence response; and beam patterning and/or steering optics configured to receive the target coordinates of the target cell, and selectively direct the photo-activating light to irradiate a target location of the target cell in the sample based on the target coordinates.

6. The method according to claim 5, wherein at least one of the photo-activation light sources comprises a pulsed laser which is focused at a specific location inside the sample for photo-activating the phototagging agent by multi-photon absorption, wherein the sample holder comprises a moveable stage configured to vary a coordinate of the laser focus in the sample along an optical axis of the microscope system based on at least one of the target coordinates of the target cell.

7. The method according to claim 6, wherein the microscope system comprises a light patterning device arranged in a light path between at least one of the image light sources and the sample holder for applying a pattern of the imaging light, wherein the microscope system is configured to reconstruct a 3D image based on structured illumination imaging or Hadamard imaging method.

8. The method according to claim 7, wherein the light patterning device is further arranged in a light path between at least one of the photo-activation light sources and the sample holder for selectively applying the photo-activating light onto the selected target cell of a two-dimensional sample.

9. The method according to claim 5, wherein the controller is configured to analyze one or more sample images to automatically identify and/or track one or more target cells based on a predetermined criterion, and control the beam patterning and/or steering optics to direct the photo-activating light to irradiate one or more target locations in the sample corresponding to the one or more target cells.

10. The method according to claim 5, wherein the microscope system comprises a sensor configured to measure a fluorescence response from cells in the sample; and a mechanism configured to physically isolate the irradiated target cell from other cells in the sample based on a difference in its fluorescence response compared to non-activated phototagging agent in the other cells.

11. The method according to claim 1, wherein the phototagging agent is cell permeable.

12. The method according to claim 11, wherein the photosensitizer moiety is configured to absorbs light of a wavelength 360 nm-420 nm, while the caged fluorophore moiety is essentially insensitive to light of a wavelength >400 nm.

13. The method according to claim 11, wherein the caged fluorophore moiety is based on a fluorophore selected from the group consisting of fluorone-based fluorophores, coumarin-based fluorophores, cyanine-based fluorophores, DCDHF-based fluorophores, and combination thereof; and the photosensitizer moiety is based on a photosensitizer selected from the group consisting thioxanthones, thiopyrylium, eosin, acridinedione derivatives, and combinations thereof.

14. The method according to claim 11, wherein the phototagging agent has a structure according to any one of structures I, II, III, or IV,

I

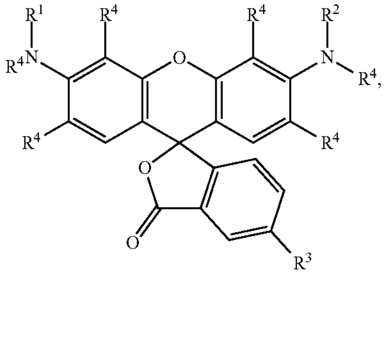

-continued

II

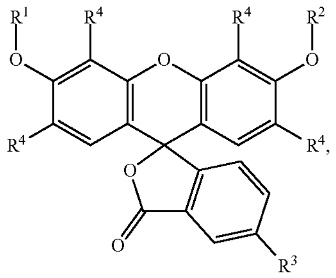

III

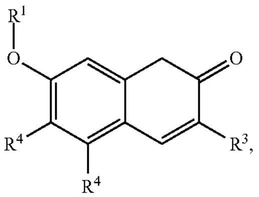

or

IV

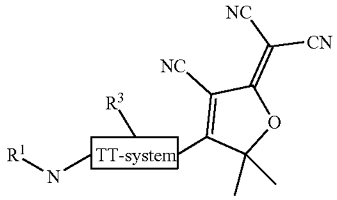

wherein a core of said structure represents the caged fluorophore moiety, $R^1$ and $R^2$ individually represent a cage moiety and individually comprise a photo-liable group, $R^3$ represents the photosensitizer moiety, and each $R^4$ is individually selected from the group consisting of H, halide, $C_1$-$C_6$-alkyl, $C_1$-$C_6$-alkoxy, $C_1$-$C_6$-alkylenes and $C_1$-$C_6$-alkoxylenes;

wherein $R^3$ comprises the structure V,

V

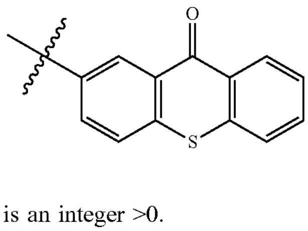

wherein n is an integer >0.

15. The method according to claim 11, wherein the phototagging agent is selected from the group consisting of chemical compounds A, B and C Chemical compound A

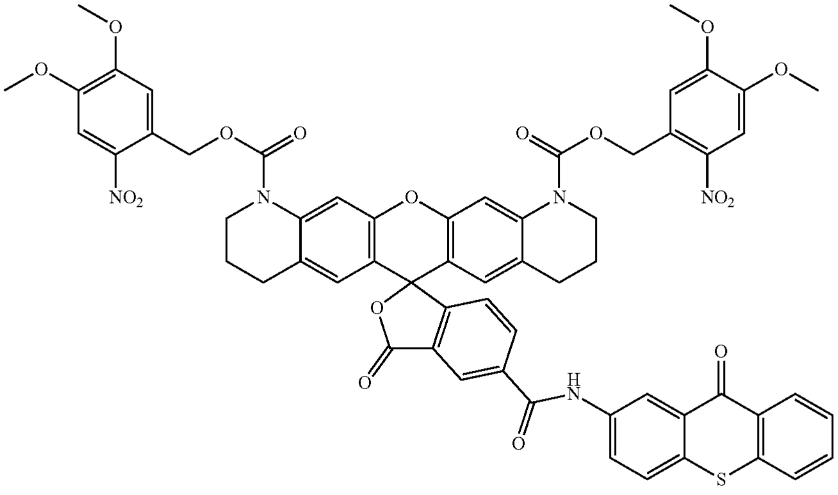

Chemical compound B

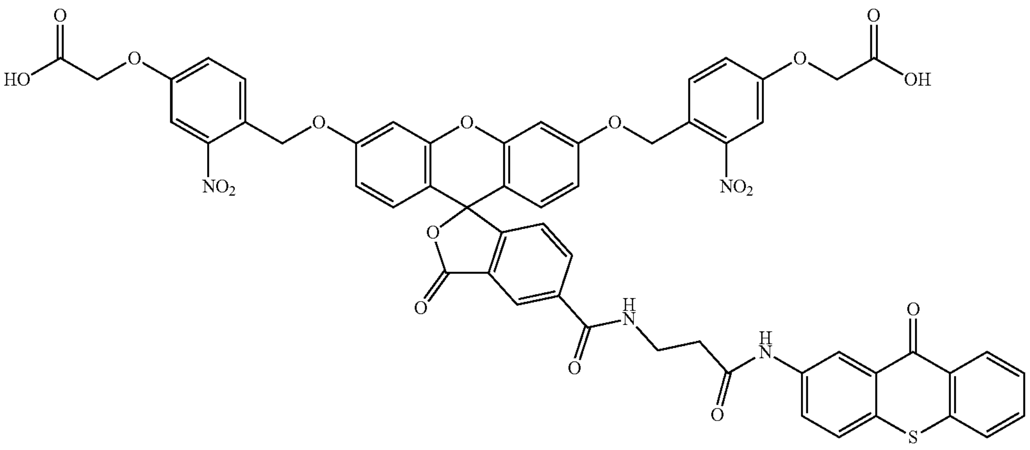

Chemical compound C

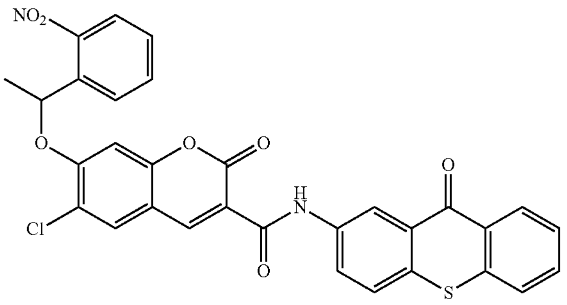

and combinations thereof.

16. The method of claim 1, wherein the phototagging agent is formed by a chemical compound inside the cells of the sample, the chemical compound comprising a caged fluorophore moiety conjugated to a photosensitizer moiety.

17. The method of claim 16, wherein the photosensitizer moiety absorbs light of a wavelength 360 nm-420 nm, while the caged fluorophore moiety is insensitive to light of a wavelength >400 nm.

18. The method of claim 16, wherein the caged fluorophore moiety is based on a fluorophore selected from the group consisting of fluorone-based fluorophores, coumarin-based fluorophores, cyanine-based fluorophores, DCDHF-based fluorophores, and combination thereof; and the photosensitizer moiety is based on a photosensitizer selected from the group consisting thioxanthones, thiopyrylium, eosin, acridinedione derivatives, and combinations thereof.

19. The method of claim 16, wherein the chemical compound has a structure according to any one of structures I, II, III or IV,

I

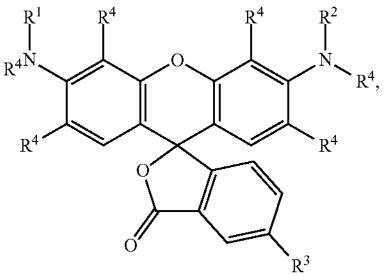

II

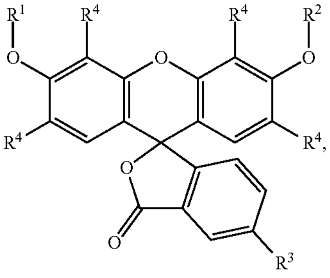

III

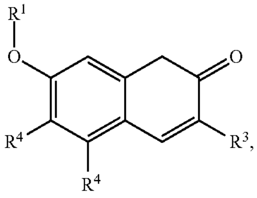

or

-continued

IV

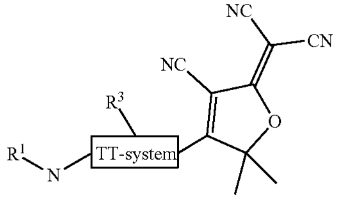

wherein a core of said structure represents the caged fluorophore moiety, $R^1$ and $R^2$ individually represent a cage moiety and individually comprise a photo-liable group;

$R^3$ represents the photosensitizer moiety, and each $R^4$ is individually selected from the group consisting of H, halide, $C_1$-$C_6$-alkyl, $C_1$-$C_6$-alkoxy, $C_1$-$C_6$-alkylenes and $C_1$-$C_6$-alkoxylenes;

wherein $R^3$ comprises the structure V,

V

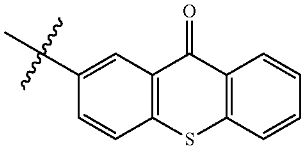

wherein n is an integer >0.

20. The method of claim 16, wherein the chemical compound is selected from the group consisting of chemical compounds A, B and C Chemical compound A

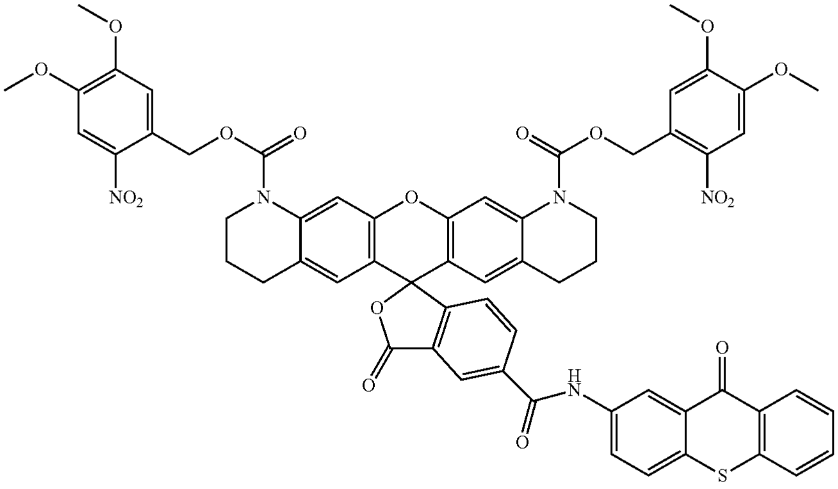

-continued
Chemical compound B
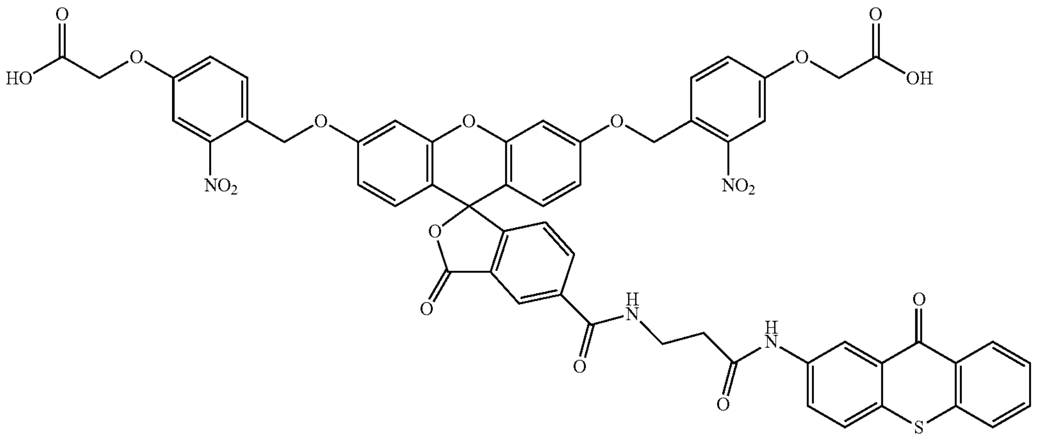
Chemical compound C
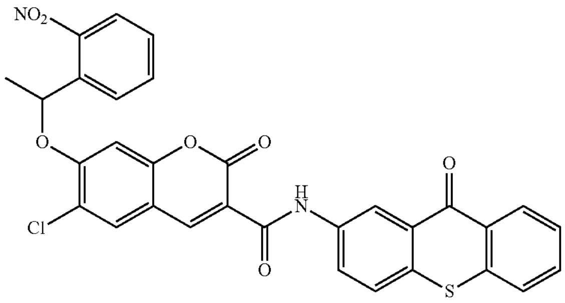
and combinations thereof.
* * * * *